(12) United States Patent
Oki et al.

(10) Patent No.: US 12,157,772 B2
(45) Date of Patent: Dec. 3, 2024

(54) PROPHYLACTIC AGENT, ONSET-SUPPRESSING AGENT OR THERAPEUTIC AGENT FOR PROGRESSIVE IMMUNE DEMYELINATING DISEASES

(71) Applicant: NATIONAL CENTER OF NEUROLOGY AND PSYCHIATRY, Kodaira (JP)

(72) Inventors: Shinji Oki, Kodaira (JP); Takashi Yamamura, Kodaira (JP)

(73) Assignee: NATIONAL CENTER OF NEUROLOGY AND PSYCHIATRY, Tokyo (JP)

( * ) Notice: Subject to any disclaimer, the term of this patent is extended or adjusted under 35 U.S.C. 154(b) by 48 days.

(21) Appl. No.: 17/149,570

(22) Filed: Jan. 14, 2021

(65) Prior Publication Data

US 2021/0230282 A1 Jul. 29, 2021

Related U.S. Application Data

(63) Continuation of application No. 16/463,826, filed as application No. PCT/JP2017/042629 on Nov. 28, 2017, now abandoned.

(30) Foreign Application Priority Data

Nov. 29, 2016 (JP) ................. 2016-231364

(51) Int. Cl.
| | | |
|---|---|---|
| C07K 16/28 | (2006.01) | |
| A61P 25/00 | (2006.01) | |
| C12Q 1/02 | (2006.01) | |
| A61K 45/06 | (2006.01) | |

(52) U.S. Cl.
CPC .......... *C07K 16/2866* (2013.01); *A61P 25/00* (2018.01); *C12Q 1/02* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 9,035,029 | B2 | 5/2015 | Singh et al. |
| 9,730,923 | B2 | 8/2017 | Lagarde et al. |
| 10,385,134 | B2 | 8/2019 | Singh et al. |
| 2002/0192212 | A1 | 12/2002 | Imai et al. |
| 2011/0245261 | A1 | 10/2011 | Lagarde et al. |

FOREIGN PATENT DOCUMENTS

| | | |
|---|---|---|
| JP | 2009/509943 A | 3/2009 |
| WO | WO 2007/036033 A1 | 4/2007 |
| WO | WO 2013/130381 A1 | 9/2013 |
| WO | WO 2016/002827 A1 | 1/2016 |
| WO | WO 2016/114386 A1 | 7/2016 |

OTHER PUBLICATIONS

Espacenet Machine Translation of WO 2016/002827 A1 (published Jan. 2016) claims, downloaded Sep. 13, 2022.*
Espacenet Machine Translation of WO 2016/002827 A1 (published Jan. 2016) specification, downloaded Sep. 13, 2022.*
Raveney, et al: "Eomesodermin-express T-helper cells are essential for chronic neuroinflammation", Nature Communications; Oct. 5, 2015; vol. 6(1); pp. 8437; doi:10.1038/ncomms9437.
International Search Report mailed Mar. 6, 2018 for PCT Application No. PCT/JP2017/042629, 4 pages. (English translation).
International Preliminary Report on Patentability mailed Jun. 13, 2019 for PCT Application No. PCT/JP2017/042629, 11 pages. (English translation).
Cao, et al., "ZBTB20 is required for anterior pituitary development and lactotrope specification", Nature Communications Apr. 2016, vol. 7:11121, pp. 1-13.
Comi: "Disease-modifying treatments for progressive multiplesclerosis", Multiple Sclerosis Journal Aug. 2013, vol. 19, No. 11, pp. 1428-1436.
Dijkstra, et al: "Therapeutic Effect of the D2-Dopamine agonist Bromocriptine on acute and relapsing experimental allergic encephalomyelitis", Psychoneuroendocrinology 1994, vol. 19, No. 2, pp. 135-142.
Esquifino, et al: "Experimental allergic encephalomyelitis in pituitary-grafted Lewis rats", Journal of Neuroinflammation 2006, vol. 3, No. 20, pp. 1-5.
Koch, et al: "Treatment trials in progressive MS-current challenges and future directions", Nature Reviews Neurology Sep. 2013, vol. 9, pp. 496-503.
Lassmann, et al: "Progressive multiple sclerosis: pathology and pathogenesis", Nature Reviews Neurology Nov. 2012, vol. 8, pp. 647-656.
Mao, et al: "Is multiple sclerosis a mitochondrial disease?", Biochimica et Biophysica Acta 2010, vol. 1802, pp. 66-79.
McCoy, et al: "Orphan nuclear receptor NR4A2 induces transcription of the immunomodulatory peptidehormone prolactin", Journal of Inflammation 2015, vol. 12, No. 13, pp. 1-11.
Nakatsuji: "Routine care, actual treatments of multiple sclerosis and similar diseases, treatment of secondary progressive multiple sclerosis Spms)", MS Frontier 2013, vol. 2, No. 1, pp. 30-34. (with English translation).
Communication forwarding the partial European Search Report for European Patent Application No. 17876119.3 dated May 25, 2020, 9 pages.
Wollberg, et al., "Pharmacological Inhibition of the Chemokine Receptor CX3CR1 Attenuates Disease in a Chronic-Relapsing Rat Model for Multiple Sclerosis" Proceedings of the National Academy of Sciences USA , Apr. 8, 2014; vol. 111, No. 14, pp. 5409-5414; XP055691834.

(Continued)

*Primary Examiner* — Marianne P Allen
(74) *Attorney, Agent, or Firm* — Squire Patton Boggs (US) LLP

(57) ABSTRACT

The present invention provides a prophylactic agent, onset-suppressing agent, or therapeutic agent for progressive immune demyelinating diseases comprising, as an active ingredient, a substance capable of suppressing or inhibiting production of prolactin.

1 Claim, 40 Drawing Sheets

(56) References Cited

OTHER PUBLICATIONS

Koutoku Aihara, et al: "The novel antipsychotic aripiprazole is a partial agonist at short and long isoforms of D2 receptors linked to the regulation of adenylyl cyclase activity and prolactin release", Brain Research; Dec. 31, 2004; vol. 1003, No. 1-2, pp. 9-17.
BioLegend Purified Anti-Human CX3CR1 Antibody, Catalog #341602 product information (2 pages), revised Nov. 30, 2012.
Anonymous, "Types of MS URL:https://www.nationalmssociety.org/What-is-MS/Types-of-MS ", National Multiple Sclerosis Society, Jul. 20, 2010; pp. 1-6.
Lassmann, et al., "Multiple sclerosis: experimental models and reality", Acta Neuropathologica 2017 (published online Oct. 20, 2016); vol. 133(2); pp. 223-244.
Communication pursuant to Article 94(3) EPC dated Jun. 22, 2023 forwarding the examination report for European Patent Application No. 17876119.3; pp. 1-8.

* cited by examiner

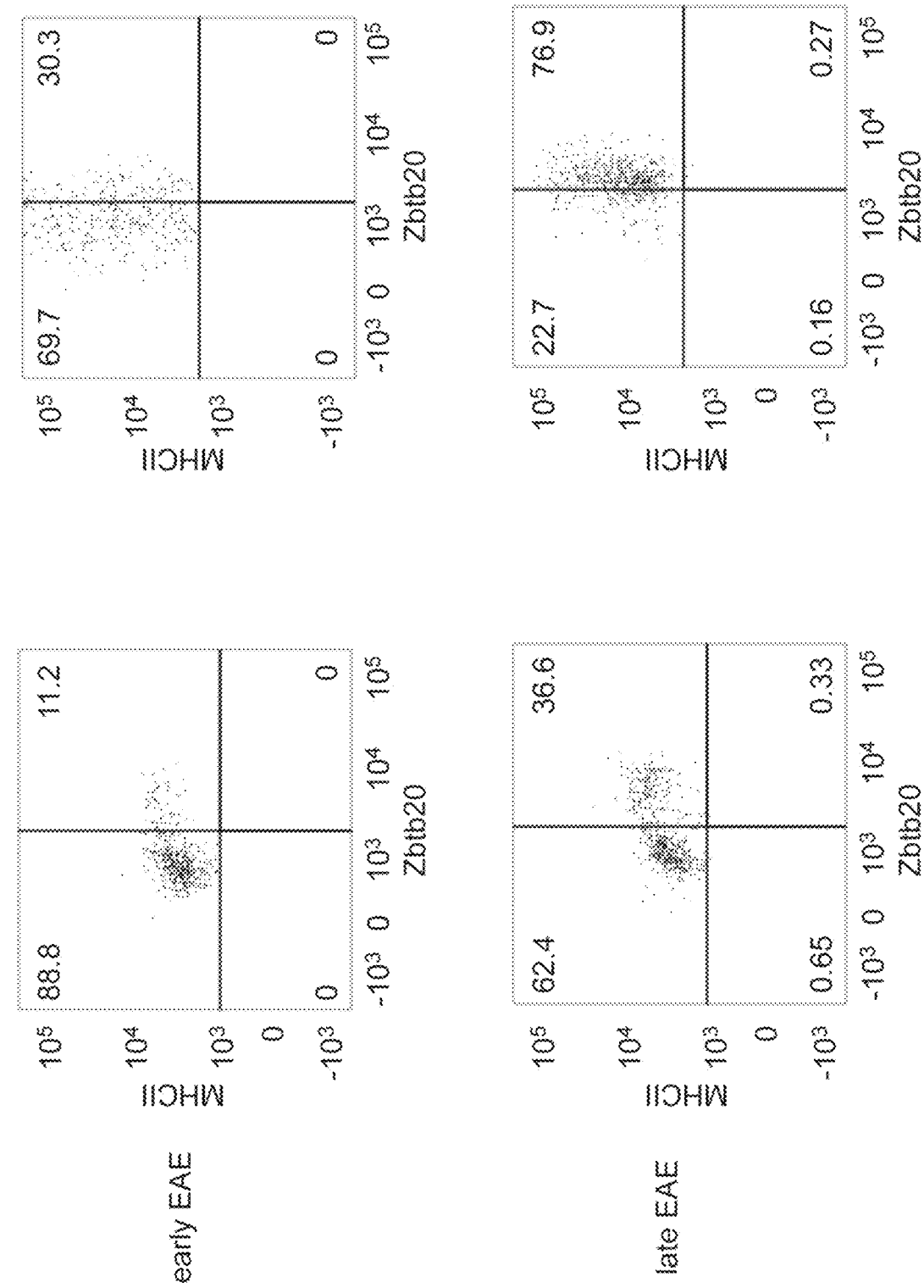

PROPHYLACTIC AGENT, ONSET-SUPPRESSING AGENT OR THERAPEUTIC AGENT FOR PROGRESSIVE IMMUNE DEMYELINATING DISEASES

TECHNICAL FIELD

The present invention relates to a prophylactic agent, onset-suppressing agent, or therapeutic agent for progressive immune demyelinating diseases.

BACKGROUND ART

Multiple sclerosis (MS) is one of autoimmune diseases and a disease in which multiple inflammations targeting myelin sheaths and nerve axons are triggered, resulting in nerve conduction disorders caused by widespread demyelination. When multiple sclerosis pathology is advanced, severe neurological symptoms such as motor impairment and visual disturbance appear.

Multiple sclerosis includes: relapsing-remitting MS (RR-MS) having repeated acute exacerbation and remission; and progressive MS. It has been known that the progressive MS includes: primary progressive MS (PP-MS); secondary progressive MS (SP-MS) in which RR-MS pathology continues for a certain period and then progresses into advanced pathology; and progressive relapsing MS (PR-MS) in which the pathology progresses with repeated relapse (Non Patent Literatures 1 to 3).

Type-1 interferons, anti-inflammatory agents, and immunosuppressive agents have been known as disease-modifying drugs (DMDs) for RR-MS. Unfortunately, use of DMDs for RR-MS cannot exert effects on progressive MS and effective DMDs for progressive MS are not currently known. As a treatment strategy for progressive MS, symptomatic treatment such as intraspinal injection of baclofen or dosing of persistent 4-aminopyridine preparation occupies an important position.

To date, the mechanism of producing progressive MS pathology has not been revealed, including whether the mechanism is identical to or different from the mechanism of producing RR-MS pathology. Meanwhile, Non Patent Literature 4 reports that in the central nervous system (CNS) of each SP-MS patient, a plurality of cells and tissues are damaged and the damage spreads not only into white matter but also into gray matter. In addition, Non Patent Literature 4 reports that in the brain of patients with multiple sclerosis, the expression level of PAR2 receptor, which belongs to the PAR (Protease-activated receptors) receptor family, is changed, indicating that the PAR2 receptors participate in neuroinflammatory symptoms.

The present inventors have found that in NR4A2-deficient mice, in which monophasic experimental autoimmune encephalomyelitis (EAE) is induced, EAE pathology usually accompanied by quadriplegia is not observed at the early stage of the induction; but at the late stage of the induction (about 28 days after the induction), EAE pathology (hereinafter, sometimes referred to as "late-stage EAE pathology") is observed; and this late-stage EAE pathology can be a model for progressive MS pathology (Patent Literature 1). In addition, the present inventors have considered that the late-stage EAE pathology including neurodegeneration results from persistent neuronopathy caused by stimulation-dependent release of granzyme B and have found that inhibition of PAR1 receptor by using, for instance, a PAR1 receptor antagonist causes the late-stage EAE pathology to improve (Patent Literature 2).

CITATION LIST

Patent Literature

Patent Literature 1: WO 2016/002827
Patent Literature 2: WO 2016/114386

Non Patent Literature

Non Patent Literature 1: Nature Reviews Neurology 2012, 8, 647-656.
Non Patent Literature 2: Nature Reviews Neurology 2013, 9, 496-503.
Non Patent Literature 3: Multiple Sclerosis Journal 2013, 19: 1428-1436.
Non Patent Literature 4: Biochimica et Biophysica Acta 1802 (2010), 66-79.

SUMMARY OF INVENTION

Technical Problem

The present invention has been made in light of these situations and the main purpose thereof is to provide a prophylactic agent, onset-suppressing agent, or therapeutic agent for progressive immune demyelinating diseases. Another purpose of the present invention is to provide a method for preventing or suppressing a progression into progressive immune demyelinating diseases.

Solution to Problem

The present inventors have discovered that in the late-stage EAE pathology of NR4A2-deficient mice, expression of Eomes molecule in Th cells is induced by stimulation from CNS-derived antigen-presenting cells and prolactin produced from the antigen-presenting cells can promote induction of the Eomes molecule expression. The present invention is based on these new findings. Note that it has been known that prolactin can be produced from not only the pituitary but also brain tissues other than the pituitary, the mammary gland, mammary papilla tissues, placenta, uterus, immune tissues (e.g., lymphocytes, the thymus, the spleen), etc. The above tissue-derived prolactin is distinct from the pituitary-derived prolactin and is also called ectopic prolactin.

Specifically, the present invention provides the following (1) to (15).

(1) A prophylactic agent, onset-suppressing agent, or therapeutic agent for progressive immune demyelinating diseases comprising, as an active ingredient, a substance capable of suppressing or inhibiting production of prolactin.

(2) The prophylactic agent, onset-suppressing agent, or therapeutic agent for progressive immune demyelinating diseases according to (1), wherein the substance comprises a substance capable of suppressing or inhibiting generation of Zbtb20.

(3) The prophylactic agent, onset-suppressing agent, or therapeutic agent for progressive immune demyelinating diseases according to (1), wherein the substance comprises a dopamine receptor agonist or a dopamine receptor partial agonist.

(4) The prophylactic agent, onset-suppressing agent, or therapeutic agent for progressive immune demyelinating diseases according to any one of (1) to (3), wherein the progressive immune demyelinating disease is secondary progressive multiple sclerosis.

(5) A method for preventing or suppressing a progression into progressive immune demyelinating diseases, comprising administering, to a subject, a substance capable of suppressing or inhibiting production of prolactin.

(6) The method according to (5), wherein the substance comprises a substance capable of suppressing or inhibiting generation of Zbtb20.

(7) The method according to (5), wherein the substance comprises a dopamine receptor agonist or a dopamine receptor partial agonist.

(8) The method according to any one of (5) to (7), wherein the progressive immune demyelinating disease is secondary progressive multiple sclerosis.

(9) Use of a substance capable of suppressing or inhibiting production of prolactin in the manufacture of a prophylactic agent, onset-suppressing agent, or therapeutic agent for progressive immune demyelinating diseases.

(10) The use according to (9), wherein the substance comprises a substance capable of suppressing or inhibiting generation of Zbtb20.

(11) The use according to (9), wherein the substance comprises a dopamine receptor agonist or a dopamine receptor partial agonist.

(12) The use according to any one of (9) to (11), wherein the progressive immune demyelinating disease is secondary progressive multiple sclerosis.

(13) A prophylactic agent, onset-suppressing agent, or therapeutic agent for progressive immune demyelinating diseases comprising, as an active ingredient, a substance capable of suppressing or inhibiting activation of CX3CR1 receptor.

(14) The prophylactic agent, onset-suppressing agent, or therapeutic agent for progressive immune demyelinating diseases according to (13), wherein the substance is an anti-CX3CR1 antibody or an antigen-binding fragment thereof.

(15) A method of collecting data for diagnosing a progression into progressive immune demyelinating diseases comprising: collecting microglia from a human subject; and measuring an expression level of at least one of IL-9, IFN-α, and IFN-β1.

Advantageous Effects of Invention

The present invention makes it possible to provide a prophylactic agent, onset-suppressing agent, or therapeutic agent for progressive immune demyelinating diseases and to provide a method for preventing or suppressing a progression into progressive immune demyelinating diseases.

BRIEF DESCRIPTION OF DRAWINGS

FIG. 8 is graphs showing the effects of culturing in the co-presence of prolactin on Eomes expression.

FIG. 10 is cytograms showing the Zbtb20 protein expression in antigen-presenting cells infiltrated into the CNS of each NR4A2-deficient mouse in which monophasic EAE was induced.

FIG. 33 is graphs showing Zbtb20 protein expression under culturing in the presence of each different cytokine.

FIG. 36 is graphs showing the changes in expression of each different cytokine during the course of progression of EAE pathology.

FIG. 37 is cytograms and graphs showing expression of prolactin gene or Zbtb20 gene under culturing in the presence of microglia collected from each mouse having the late-stage EAE pathology.

DESCRIPTION OF EMBODIMENTS

Definitions

Figure 1:
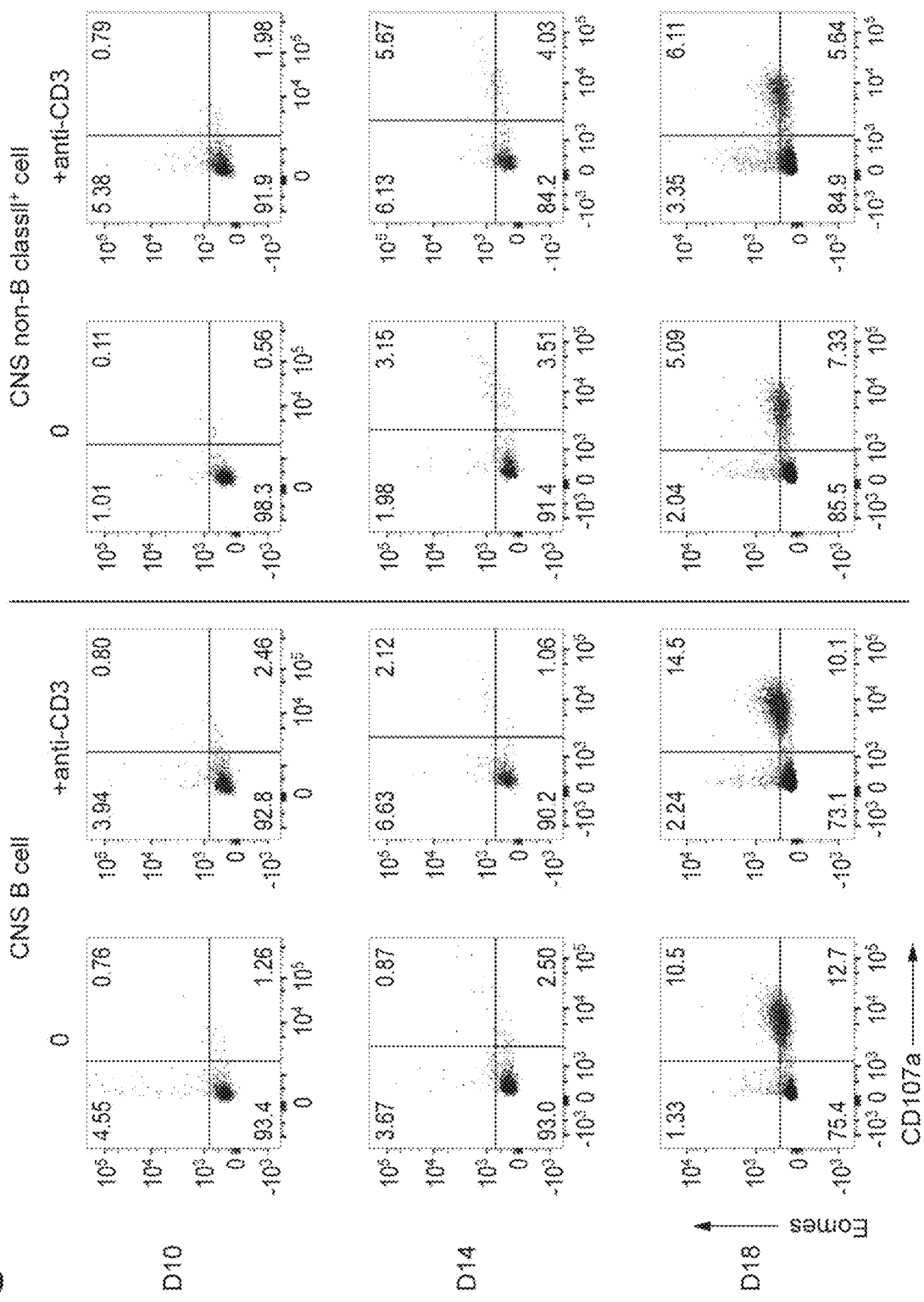
FIG. 1 is cytograms showing expressions of CD107a and Eomes on and in Th cells co-cultured with antigen-presenting cells (CD19$^+$ B cells or non-B/class II$^+$ cells) infiltrated into the CNS of each NR4A2-deficient mouse in which monophasic EAE was induced.

As used herein, the "progressive immune demyelinating diseases" means diseases caused by myelin sheath impairment resulting from an immune reaction, namely a persistently progressive diseases without remission. The progressive immune demyelinating disease is preferably CNS progressive immune demyelinating diseases. Examples of the progressive immune demyelinating diseases include progressive multiple sclerosis such as PP-MS, SP-MS, and PR-MS.

NR4A2 gene is also referred to as Nurr1 gene, NOT gene, or RNR1 gene and is a kind of orphan nuclear receptor. The major expression site of NR4A2 gene lies in the central nervous system and the NR4A2 gene is strongly expressed, in particular, in the ventral mesencephalon, brain stem, and spinal cord. Meanwhile, expression of NR4A2 can be induced in response to prostaglandins, growth factors, inflammatory cytokines, and/or T-cell receptor cross-linking, and NR4A2 can directly bind to DNA, in a ligand-dependent or -independent manner, to regulate transcription. The accession number of human NR4A2 gene transcript in the NCBI Reference Sequences is NM_006186.3.

Eomes gene is also called Eomesodermin or Tbr2, is a kind of T-box transcription factor, and is a protein participating in development and differentiation of vertebrates. It has been known that Eomes gene is expressed in CD8$^+$ T cells (cytotoxic T lymphocytes; CTL) and NK cells. In addition, it is also known that Eomes gene can directly induce expression of perform and granzyme B. The accession numbers of human Eomes gene transcripts in the NCBI Reference Sequences are NM_001278182.1 (variant 1), NM_005442.3 (variant 2), and NM_001278183.1 (variant 3).

Zbtb20 is a protein belonging to one of subfamilies of C2H2 Kruppel-like zinc finger proteins and BTB/POZ domain-containing zinc finger proteins. In addition, Zbtb20 can bind to a promoter of prolactin gene and can thus promote transcriptional activation of prolactin. Zbtb20 is highly expressed in all mature endocrine cell types in the anterior pituitary gland. When Zbtb20 is deficient, expression and secretion of prolactin decrease markedly.

[Prophylactic Agent, Onset-Suppressing Agent, or Therapeutic Agent for Progressive Immune Demyelinating Diseases]

A prophylactic agent, onset-suppressing agent, or therapeutic agent for progressive immune demyelinating diseases according to a first embodiment of the present invention comprises, as an active ingredient, a substance capable of suppressing or inhibiting production of prolactin.

The progressive immune demyelinating disease is preferably CNS progressive immune demyelinating diseases and more preferably secondary progressive multiple sclerosis (SP-MS).

Examples of the substance capable of suppressing or inhibiting production of prolactin include: expression suppressors capable of suppressing expression of prolactin gene; dopamine receptor agonists; dopamine receptor partial agonists; dopamine reuptake inhibitors; dopamine degrading enzyme inhibitors; dopamine analogs; and substances capable of suppressing or inhibiting generation of Zbtb20. It is preferable that each dopamine receptor agonist or partial agonist is a dopamine D2 receptor agonist or partial agonist.

Each expression suppressor capable of suppressing expression of prolactin gene may be a substance capable of suppressing a prolactin from functioning as a protein. Examples of the expression suppressor include: substances capable of suppressing expression of prolactin gene at a transcription or translation level; and substances capable of suppressing functional expression while binding to a functional site of prolactin.

Examples of the substances capable of suppressing expression of prolactin gene at a transcription or translation level include nucleic acids, peptides, sugars or glycoproteins, and low-molecular-weight compounds with a molecular weight of 1000 or less, that can suppress gene expression of prolactin. Examples of the nucleic acids capable of suppressing gene expression of prolactin include at least one kind selected from the group consisting of anti-sense oligonucleotides, siRNAs, shRNAs, miRNAs, and ribozymes for prolactin gene.

Examples of the substances capable of suppressing functional expression while binding to a functional site of prolactin include anti-prolactin antibodies (e.g., neutralizing antibodies) or antigen-binding fragments thereof.

Each expression suppressor capable of suppressing expression of prolactin may be designed and produced, by known procedures in the art, based on information on the genome sequence and mRNA sequence of prolactin gene, the sequence and conformation of prolactin protein, etc.

Examples of the dopamine receptor agonists include dopamine, apomorphine, bromocriptine, cabergoline, ciladopa, dihydrexidine, dinapsoline, doxanthrine, epicriptine, lisuride, pergolide, piribedil, pramipexole, propylapomorphine, quinagolide, talipexole, ropinirole, rotigotine, roxindole, and sumanirole.

Examples of the dopamine receptor partial agonists include aripiprazole, brexpiprazole, phencyclidine, salvinorin A, and quinpirole.

Examples of the dopamine reuptake inhibitors include altropane, amfonelic acid, amineptine, BTCP, DBL-583, difluoropin, GBR-12783, GBR-12935, GBR-13069, GBR-13098, GYKI-52895, lometopane, methylphenidate, RTI-229, and vanoxerine.

Examples of the dopamine degrading enzyme inhibitors include: monoamine oxidase B inhibitors such as selegiline, zonisamide; and catechol-o-methyltransferase (COMT) inhibitors such as entacapone.

Examples of the dopamine analogs include L-dopa (levodopa, L-3,4-dihydroxyphenylalanine) and droxidopa (L-threo-dihydroxyphenylserine).

Each expression suppressor capable of suppressing expression of Zbtb20 gene may be a substance capable of suppressing the functioning of ZBtb20 as a protein. Examples of the expression suppressor include: substances capable of suppressing expression of Zbtb20 gene at a transcription or translation level; and substances capable of suppressing functional expression while binding to a functional site of Zbtb20. Examples of the substances capable of suppressing expression of Zbtb20 gene at a transcription or translation level include nucleic acids, peptides, sugars or glycoproteins, and low-molecular-weight compounds with a molecular weight of 1000 or less, that can suppress gene expression of Zbtb20. Examples of the nucleic acids capable of suppressing gene expression of Zbtb20 include at least one kind selected from the group consisting of anti-sense oligonucleotides, siRNAs, shRNAs, miRNAs, and ribozymes for Zbtb20 gene. Examples of the substances capable of suppressing functional expression while binding to a functional site of Zbtb20 include nucleic acids, peptides, sugars or glycoproteins, low-molecular-weight compounds with a molecular weight of 1000 or less, and anti-Zbtb20 antibodies (e.g., neutralizing antibodies) or antigen-binding fragments thereof that can suppress functional expression while binding to a functional site of Zbtb20.

Each expression suppressor capable of suppressing expression of Zbtb20 may be designed and produced, by known procedures in the art, based on information on the genome sequence and mRNA sequence of Zbtb20 gene, the sequence and conformation of Zbtb20 protein, etc. The expression suppressors capable of suppressing expression of Zbtb20 may be, for instance, substances capable of inhibiting or suppressing a microRNA122/CUX1/microRNA214/ZBTB20 pathway. It has been known that forced expression of microRNA214 or microRNA214 causes expression of Zbtb20 gene to be suppressed (Kojima et al. Nature communications 2011, 2: 338, 1-10). In addition, the expression suppressors capable of suppressing expression of Zbtb20 may be, for instance, substances capable of suppressing expression of LMP2A (Latent membrane protein 2A) and/or IRF4 (Interferon regulatory factor 4). It has been known that in LMP2A-expressing B cells, expression of Irf4 and Zbtb20 genes is enhanced; and IRF4 protein encoded by Irf4 binds to a Zbtb20 promoter, thereby enhancing expression of Zbtb20 gene (Minamitani et al. Proc. Natl. Acad. Sci. 2015, 112, 37, 11612-11617).

The content of the above active ingredient (substance capable of suppressing or inhibiting production of prolactin) in the prophylactic agent, onset-suppressing agent, or therapeutic agent for progressive immune demyelinating diseases according to this embodiment is not particularly limited; and for instance, the content may be from 0.001 to 100 mass % based on the total amount of the prophylactic agent, onset-suppressing agent, or therapeutic agent for progressive immune demyelinating diseases.

The prophylactic agent, onset-suppressing agent, or therapeutic agent for progressive immune demyelinating diseases may be constituted only of the above active ingredient or may contain, in addition to the above active ingredient, an additional drug usable for multiple sclerosis prophylactic, onset-suppressing, or therapeutic purposes; and/or an additive(s) usually used in the technical field of formulation, such as an excipient, a buffering agent, a stabilizer, an antioxidant, a binder, a disintegrating agent, a filler, an emulsifier, and/or a flow modifying additive. In addition, it is preferable that the above additional drug exerts the therapeutic efficacy by a mechanism different from the one for suppressing or inhibiting signal transduction starting from the prolactin receptor.

Examples of the additional drug include voltage-dependent sodium channel inhibitors (e.g., lamotrigine), potassium channel blockers (e.g., fampridine), voltage-dependent calcium channel suppressors (e.g., gabapentin), siponimod (BAF312), HMG-CoA inhibitors (e.g., statins such as simbastatin), SIP receptor antagonists (e.g., fingolimod (FTY720), c-kit receptor inhibitors (e.g., masitinib), MIS416, toeluna, potassium-sparing diuretics (e.g., amiloride), riluzole, phosphodiesterase inhibitors (e.g., ibudilast (MN-166)), cyclophosphamide, steroids (e.g., methylprednisolone, prednisone), topoisomerase II inhibitors (e.g., mitoxantrone), ELND002, MD1003, ritalin, quetiapine fumarate, NMDA receptor inhibitors (e.g., memantine), tacrolimus, teriflunomide (HMR1726), BHT-3009-01, sunphenon EGCG (sunphenon epigallocatechin gallate), CS-0777, glatiramer acetate (Copoxone (registered trademark)), ONO-4641, purine metabolism antagonists (e.g., cladribine), lipoic acid, inosine, cannabis, nabiximols (Sativex (registered trademark)), erythropoietin, interferon β-1b, adrenocorticotropic hormone (ACTH), estriol, synthetic partial myelin basic protein peptides (e.g., dirucotide (MBP8298)), monoclonal anti-human CD20 antibodies (e.g., rituximab), humanized monoclonal anti-α4 integrin antibodies (e.g., natalizumab (BG00002)), monoclonal anti-CD25 antibodies (e.g., daclizumab), humanized monoclonal anti-IL-12 antibodies, monoclonal anti-IL-12/23 antibodies (e.g., ABT-874 (briakinumab)), and humanized monoclonal Nogo-A antibodies (e.g., ozanezumab, GSK1223249).

Examples of a dosage form of the prophylactic agent, onset-suppressing agent, or therapeutic agent for progressive immune demyelinating diseases according to the first embodiment include any dosage forms such as powder, pills, granules, tablets, syrups, pastilles, capsules, and injections.

The prophylactic agent, onset-suppressing agent, or therapeutic agent for progressive immune demyelinating diseases according to the first embodiment may be administered orally or parenterally. When the agent is administered to, for instance, adult human males (with a body weight of 60 kg), the daily dose of the prophylactic agent, onset-suppressing agent, or therapeutic agent for progressive immune demyelinating diseases, as a specific example of the dose, is usually from 0.0001 µg to 10000 mg/day/person in terms of the active ingredient content.

The above first embodiment may also provide a method for preventing or suppressing a progression into progressive immune demyelinating diseases comprising a step of administering, to a human subject of need, a substance capable of suppressing or inhibiting production of prolactin. For instance, the above method according to the first embodiment can prevent or suppress a progression from relapsing-remitting immune demyelinating disease to progressive immune demyelinating diseases.

A prophylactic agent, onset-suppressing agent, or therapeutic agent for progressive immune demyelinating diseases according to a second embodiment of the present invention comprises, as an active ingredient, an anti-CX3CR1 antibody or an antigen-binding fragment thereof.

The progressive immune demyelinating disease is preferably CNS progressive immune demyelinating diseases and more preferably secondary progressive multiple sclerosis (SP-MS).

The anti-CX3CR1 antibody or antigen-binding fragment thereof may be a monoclonal or polyclonal antibody. The anti-CX3CR1 antibody may be any of a mouse antibody, a rat antibody, a guinea pig antibody, a hamster antibody, a rabbit antibody, a monkey antibody, a dog antibody, a chimeric antibody, a humanized antibody, or a human antibody. The anti-CX3CR1 antibody may be chemically modified in order to improve physical properties such as blood retention. In addition, the anti-CX3CR1 antibody may be conjugated to any radionuclide or toxin, etc., in order to increase therapeutic efficacy.

The anti-CX3CR1 antibody may be a monoclonal or polyclonal antibody. In addition, the anti-CX3CR1 antibody may be any of a mouse antibody, a rat antibody, a guinea pig antibody, a hamster antibody, a rabbit antibody, a monkey antibody, a dog antibody, a chimeric antibody, a humanized antibody, or a human antibody. The anti-CX3CR1 antibody may be chemically modified in order to improve physical properties such as blood retention. In addition, the anti-CX3CR1 antibody may be conjugated to any radionuclide or toxin, etc., in order to increase therapeutic efficacy.

The antigen-binding fragment may be an antibody fragment containing an antigen-binding site of the antibody; and examples include Fab, Fab', F(ab')$_2$, scFv, and diabody.

The content of the above active ingredient (anti-CX3CR1 antibody or antigen-binding fragment thereof) in the prophylactic agent, onset-suppressing agent, or therapeutic agent for progressive immune demyelinating diseases according to this embodiment is not particularly limited; and for instance, the content may be from 0.001 to 100 mass % based on the total amount of the prophylactic agent, onset-suppressing agent, or therapeutic agent for progressive immune demyelinating diseases.

The prophylactic agent, onset-suppressing agent, or therapeutic agent for progressive immune demyelinating diseases may be constituted only of the above active ingredient or may contain, in addition to the above active ingredient, an additional drug usable for multiple sclerosis prophylactic, onset-suppressing, or therapeutic purposes; and/or an additive(s) usually used in the technical field of formulation, such as an excipient, a buffering agent, a stabilizer, an antioxidant, a binder, a disintegrating agent, a filler, an emulsifier, and/or a flow modifying additive. In addition, it is preferable that the above additional drug exerts the therapeutic efficacy by a mechanism different from the one for suppressing or inhibiting signal transduction starting from the CX3CR1 receptor. The additional drug is identical to the drug designated in the first embodiment.

Examples of a dosage form of the prophylactic agent, onset-suppressing agent, or therapeutic agent for progressive immune demyelinating diseases according to the second embodiment include any dosage forms such as powder, pills, granules, tablets, syrups, pastilles, capsules, and injections.

The prophylactic agent, onset-suppressing agent, or therapeutic agent for progressive immune demyelinating diseases according to the second embodiment may be administered orally or parenterally. When the agent is administered to, for instance, adult human males (with a body weight of 60 kg), the daily dose of the prophylactic agent, onset-suppressing agent, or therapeutic agent for progressive immune demyelinating diseases, as a specific example of the dose, is usually from 0.0001 µg to 10000 mg/day/person in terms of the active ingredient content.

The above second embodiment may also provide a method for treating progressive immune demyelinating diseases or suppressing its pathology progression, the method comprising a step of administering, to a human subject of need, an anti-CX3CR1 antibody or an antigen-binding fragment thereof.

In the above first or second embodiment, the effects of preventing progressive immune demyelinating diseases, suppressing its onset, and suppressing its pathology progression may be determined by analyzing an increase in the Eomes expression levels on the Th cell surface. Examples of the procedure for analyzing an increase in the Eomes expression levels on the Th cell surface include a method for detecting Eomes⁺CD4⁺ T cells in lymphocyte-containing body fluid. The body fluid collected from each human subject may be lymphocyte-containing body fluid. Examples of the body fluid collected from each human subject include blood and cerebrospinal fluid. The blood may be peripheral blood. The Eomes⁺CD4⁺ T cells may be detected in accordance with conventional methods in the art.

The Eomes⁺CD4⁺ T cell detection is not limited to the above and may be performed by a step of separating, in accordance with a conventional method, PBMCs from a lymphocyte-containing body fluid sample collected from a human subject and a step of causing the PBMCs to react with a labeled anti-CD3 antibody or antigen-binding fragment thereof, a labeled anti-CD4 antibody or antigen-binding fragment thereof, and a labeled anti-Eomes antibody or antigen-binding fragment thereof so as to detect Eomes⁺CD4⁺ T cells by using a flow cytometer.

The present invention also provides a method of collecting data for diagnosing a progression into progressive immune demyelinating diseases comprising: collecting microglia from a human subject; and measuring an expression level of at least one of IL-9, IFN-α, and IFN-β1.

As shown in FIG. 36, in the course of progression of EAE pathology, the expression level of IFN-α, IFN-β1, and IL-9 in microglia at the time of mid-EAE pathology increase markedly. That is, the marked increase in the gene expression level of each of these cytokines in microglia of each human subject allows for collection of data for determining progression into progressive immune demyelinating diseases.

This means that each cytokine increase is larger than a threshold set based on the gene expression level of each cytokine in microglia of each healthy adult or human subject who undoubtfully has no progression into progressive immune demyelinating diseases.

EXAMPLES

Hereinafter, the present invention will be more specifically described based on Examples. However, the present invention is not limited to the following Examples.

1. Analysis of EAE in NR4A2c KO Mice (1) Animals

Mice used were all 6 to 8 weeks old and reared under specific pathogen-free conditions. A targeting vector having NR4A2 gene flanked by loxp sequences was used to establish NR4A2$^{fl/fl}$ mice. Specifically, the NR4A2 gene flanked by loxp sequences to be introduced was injected into a C57BL/6 embryonic stem cell by microinjection. The established strain was crossed with C57BL/6 FLPe mice (Riken BioResource Research Center) and the resulting strains in which a neomycin cassette was deleted were crossed with each other to generate a homozygous NR4A2$^{fl/fl}$ C57BL/6 mouse. The resulting mouse was crossed with C57BL/6 CD4-Cre mice (Taconic Farms, Inc.) to establish CD4-specific NR4A2c KO C57BL/6 mice (C57BL/6 Cre-CD4/NR4A2$^{fl/fl}$ mice).

(2) EAE Induction (Monophasic EAE)

Equal volumes of 100 µg of a peptide corresponding to MOG$_{35-55}$ residues (synthesized in Toray Research Center, Inc., Tokyo, Japan; hereinafter, sometimes referred to as a "MOG peptide") and 1 mg of dead *M. tuberculosis* H37Ra (Difco, Kansas, USA) emulsified using Complete Freund's adjuvant were mixed and emulsified with a homogenizer to prepare MOG emulsion. The resulting MOG emulsion was injected subcutaneously in 1 to 2 sites of the back of each CD4-specific NR4A2c KO C57BL/6 mouse (Cre-CD4/NR4A2$^{fl/fl}$ C57BL/6 mouse; NR4A2c KO) and, as a control, each NR4A2$^{fl/fl}$ C57BL/6 mouse (Control) to immunize them. Further, day 0 and day 2 after the immunization, 200 µL of PBS solution containing 200 ng per mouse of pertussis toxin (List Biological Laboratories, USA) was injected intraperitoneally into each mouse.

(3) Infiltration of T Cells into Central Nervous System

From each C57BL/6 mouse (Control) and each NR4A2-deficient mouse (NR4A2c KO) in which monophasic EAE had been induced in a similar manner to the above 1.(2), the brain and the spinal cord were collected at day 10 after the induction (corresponding to the early-stage EAE pathology), day 14 after the induction (corresponding to the mid-stage EAE pathology), and day 18 after the induction (corresponding to the late-stage EAE pathology). Then, a flow cytometer was used to separate CD19⁺ B cells and non-B/class II⁺ cells infiltrated into the CNS. Specifically, each tissue was cut into small pieces, which were then further dissociated at 37° C. for 40 min in RPMI 1640 medium (manufactured by Invitrogen, Inc.) containing 1.4 mg/mL collagenase H and 100 µg/mL DNase I (manufactured by Roche Inc.). The resulting tissue homogenate was made to pass through a 70-µm cell strainer (manufactured by GE Healthcare, Inc.), and was centrifuged on a Percoll discontinuous density gradient (37%/80%) to enrich leukocytes. Next, CD19⁺ B cells or non-B/class II⁺ cells infiltrated into the CNS were sorted by FACS using a FACS ARIA II (manufactured by BD Cytometry Systems, Inc.). The respective sorted CD19⁺ B cells or non-B/class II⁺ cells were co-cultured with spleen-derived CD226⁺ Th cells for 8 h. After the culturing, a flow cytometer was used to analyze a change in the expression level of each of Eomes and CD107a in and on the Th cells recovered. As antibodies used at the sorting were an anti-CD3 antibody (manufactured by Biolegend, Inc.), an anti-Eomes antibody (manufactured by eBioscience, Inc.), and an anti-CD107a antibody (manufactured by Biolegend, Inc.).

Figure 2A:
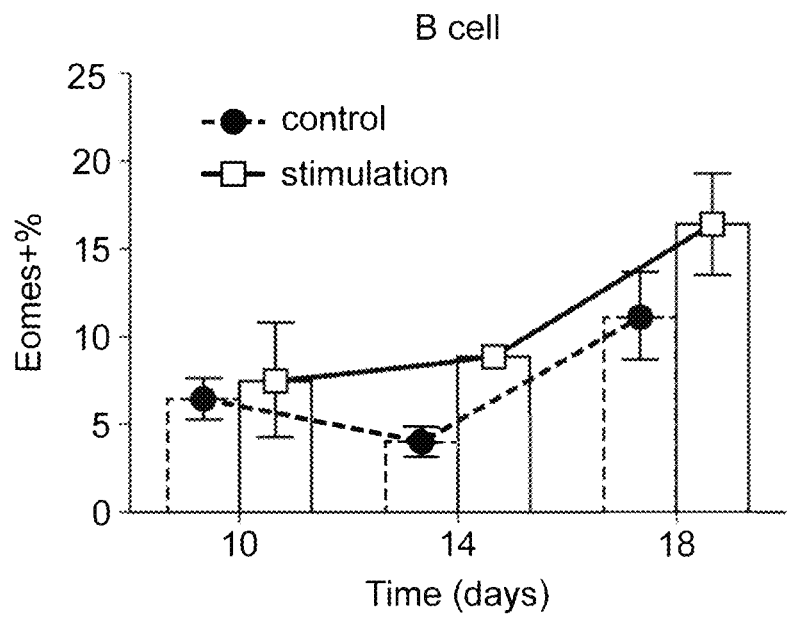
FIG. 2 is graphs showing the Eomes expression levels in Th cells co-cultured with antigen-presenting cells (CD19$^+$ B cells (FIG. 2A) or non-B/class II$^+$ cells (FIG. 2B) infiltrated into the CNS of each NR4A2-deficient mouse in which monophasic EAE was induced (summary data of FIG. 1).
Figure 2B:
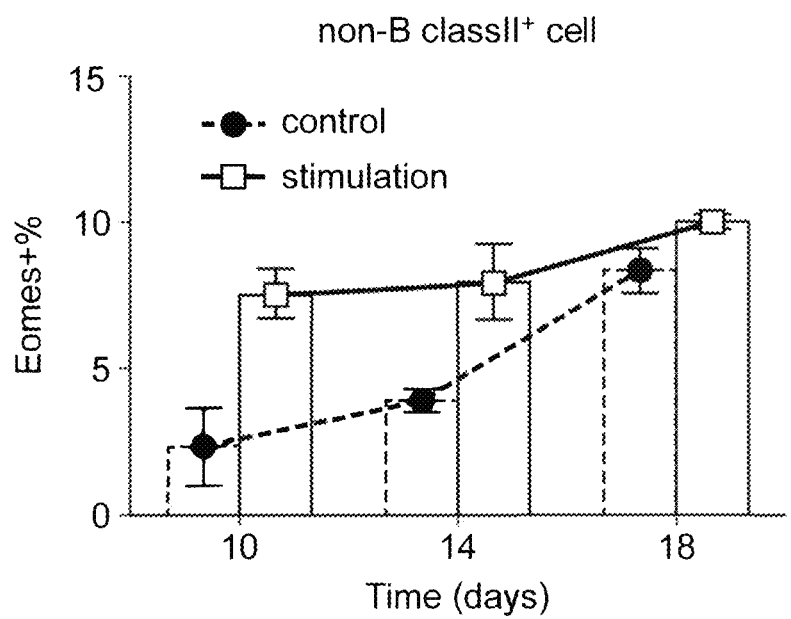

The results are shown in FIGS. 1 and 2. FIG. 1 demonstrates that in each mouse with EAE at day 18 after the induction (corresponding to the late-stage EAE pathology), the CNS-derived antigen-presenting cells have an ability of inducing marked Eomes expression in the Th cells.

(4) Eomes Expression at Each Progression Stage of EAE Pathology

Figure 3A:
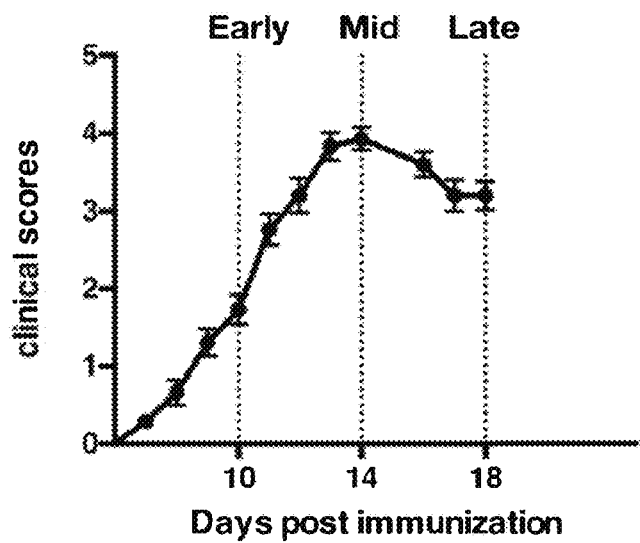
FIG. 3 is a graph showing when the brain and the spinal cord in each progression stage of EAE pathology were collected and the three dashed lines indicate the collection time points corresponding to the respective early-stage EAE pathology, mid-stage EAE pathology, and late-stage EAE pathology.
FIG. 3B is cytograms of T cells in each progression stage of EAE pathology and a graph indicating the percentage of Eomes$^+$CD4$^+$ T cells in each progression stage of EAE pathology.

From each wild-type C57BL/6 mouse in which monophasic EAE had been induced in a similar manner to the above 1.(2), the brain and the spinal cord were collected at day 10 after the induction (the early-stage EAE pathology), day 14 (the mid-stage EAE pathology), and day 18 (the late-stage EAE pathology). Then, a flow cytometer was used to separate CD4⁺ T cells infiltrated into the CNS. Note that the collection timings correspond to the Early, Mid, and Late in the graph of FIG. 3(a). Specifically, each tissue was cut into small pieces, which were then further dissociated at 37° C. for 40 min in RPMI 1640 medium (manufactured by Invitrogen, Inc.) containing 1.4 mg/mL collagenase H and 100 µg/mL DNase I (manufactured by Roche Inc.). The resulting tissue homogenate was made to pass through a 70-µm cell strainer (manufactured by GE Healthcare, Inc.), and was centrifuged on a Percoll discontinuous density gradient (37%/80%) to enrich leukocytes. Next, CD4⁺ T cells infiltrated into the CNS were sorted by FACS using a FACS ARIA II (manufactured by BD Cytometry Systems, Inc.).

Then, a flow cytometer was used to analyze a change in the Eomes expression levels in the CD4⁺ T cells separated.

As antibodies used at the detection were an anti-CD4 antibody (manufactured by Biolegend, Inc.) and an anti-Eomes antibody (manufactured by eBioscience, Inc.).

Figure 3B:
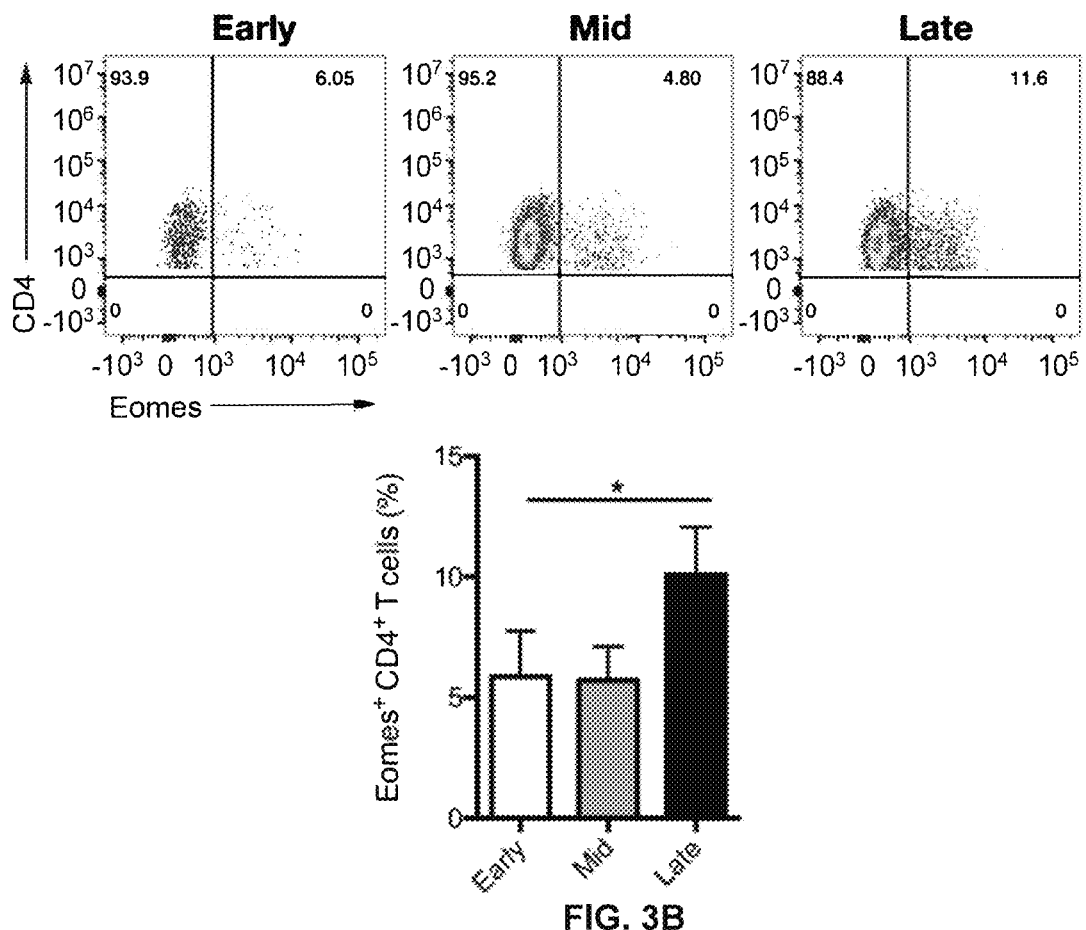

Next, each CD4$^+$ T cell was subjected to intracellular staining to measure each Eomes expression level. The results are shown in FIG. 3($b$). The graph of FIG. 3($b$) indicates the percentage (%) of Eomes$^+$ T cells with respect to the CD4$^+$ T cells in each pathology progression stage. It was observed that the percentage of Eomes$^+$CD4$^+$ T cells increased markedly in the late-stage EAE pathology.

In addition, a flow cytometer was used to separate, from the brain and the spinal cord collected, CD45$^+$ cells, CD19$^+$ B cells, and CD19$^-$ B cells infiltrated into the CNS. The separated CD45$^+$ cells, CD19$^+$ B cells, or CD19$^-$ B cells were sorted by FACS. As antibodies used at the detection were an anti-CD45 antibody (manufactured by Biolegend, Inc.), an anti-CD19 antibody (manufactured by Biolegend, Inc.), an anti-TCRβ antibody (manufactured by Biolegend, Inc.), and an anti-MHC class II antibody (manufactured by Biolegend, Inc.).

Figure 4:
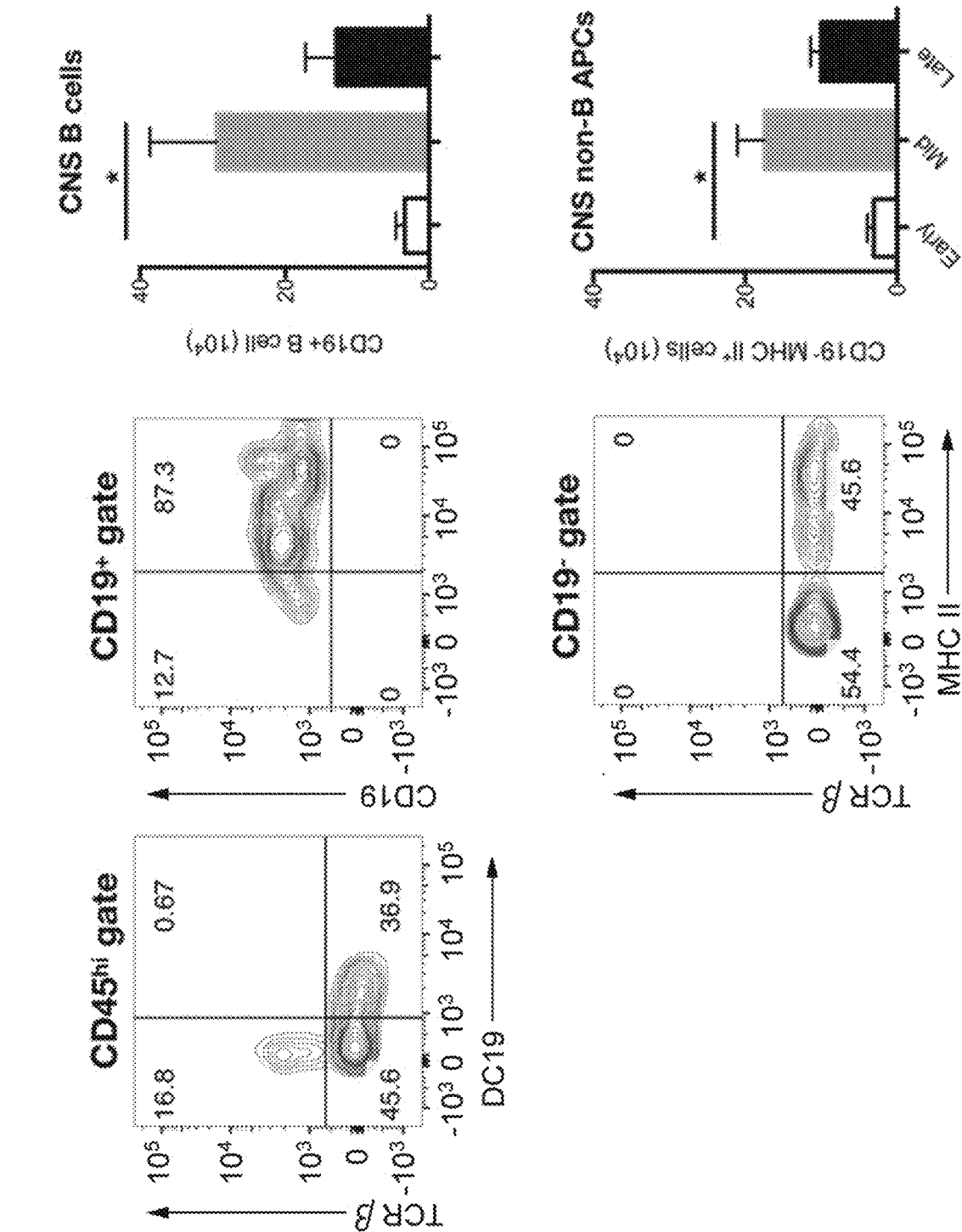
FIG. 4 is cytograms of CD19$^+$ B cells or CD19$^-$ class II$^+$ cells in each progression stage of EAE pathology and graphs indicating the percentages regarding each cell type.

The results are shown in FIG. 4. It was observed that in the mid-stage EAE pathology, infiltration of the CD19$^+$ B cells or CD19$^-$ non-B/class II$^+$ antigen-presenting cells into the CNS increased markedly; and in the late-stage EAE pathology, the numbers of these types of cells decreased when compared with those in the mid-stage EAE pathology.

(5) Gene Expression Level of Each of Prolactin and Growth Hormone in Each EAE Pathology In a similar manner to the above 1.(3), CD19$^+$ B cells or non-B/class II$^+$ cells were isolated over time from the CNS of each mouse with EAE. Then, the gene expression levels of each of prolactin (Prl) and growth hormone (Gh) were analyzed by a quantitative PCR assay. As primers for prolactin and growth hormone were used those in Mm_Prl_1_SG QuantiTect Primer Assay and Mm_Gh_1_SG QuantiTect Primer Assay (both from QIAGEN Inc.), respectively.

Figure 5A:
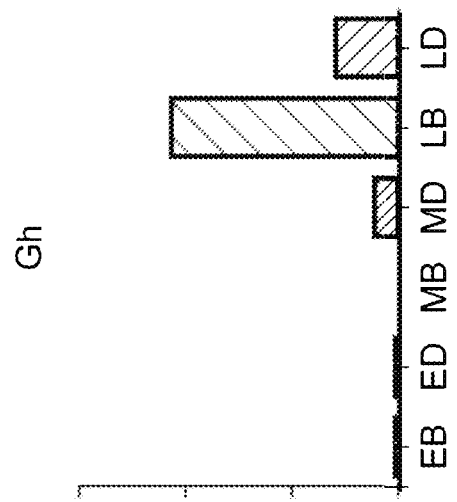
FIG. 5 is graphs showing the expression level of prolactin (FIG. 5A) or growth hormone (FIG. 5B) in antigen-presenting cells (CD19$^+$ B cells or non-B/class II$^+$ cells) infiltrated into the CNS of each NR4A2-deficient mouse in which monophasic EAE was induced.
Figure 5B:
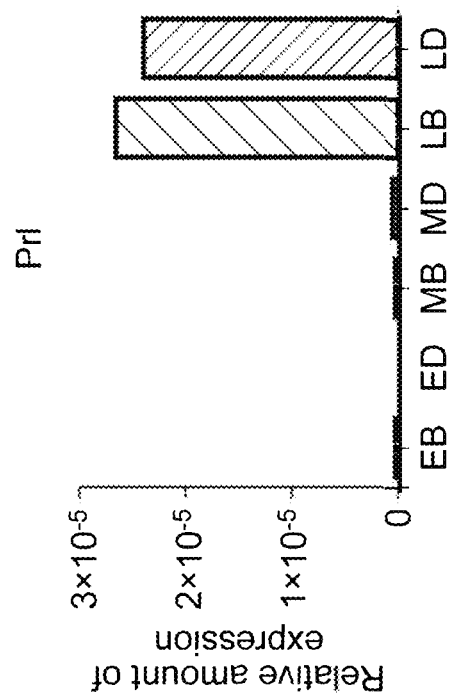

The results are shown in FIG. 5. In FIG. 5, the "EB" means CD19$^+$ B cells isolated from the early-stage EAE conditions; the "ED" means non-B/class II$^+$ cells isolated from the early-stage EAE conditions; the "MB" means CD19$^+$ B cells isolated from the mid-stage EAE conditions; the "MD" means non-B/class II$^+$ cells isolated from the mid-stage EAE conditions; the "LB" means CD19$^+$ B cells isolated from the late-stage EAE conditions; and the "LD" means non-B/class II$^+$ cells isolated from the late-stage EAE conditions. According to FIG. 5, it was observed that the expression level of each of prolactin and growth hormone increased markedly in the antigen-presenting cells derived from the CNS in the late-stage EAE conditions.

(6) Expression of Prolactin or Growth Hormone in CSF from Each Progression Stage of EAE Pathology A triple anesthesia (medetomidine, midazolam, and butorphanol) was intraperitoneally (ip) administered to anesthetize each mouse. The mice used included intact mice, mice with the early-stage EAE pathology, mice with the mid-stage EAE pathology, and mice with the late-stage EAE pathology. The skin of the occipital region in each mouse was cut like an arrowhead; the subcutaneous tissue and muscles were removed carefully; and a surface of dura mater covering cisterna magna was exposed. A glass capillary was put into the exposed dura mater for paracentesis and CSF was collected by utilizing a capillary phenomenon. Each CSF obtained was stored in a freezer at −80° C.

Then, a Luminex system (manufactured by Luminex Corporation) was used each to measure protein expression levels of prolactin (PRL) or growth hormone (GH) in each CSF collected.

Figure 6:
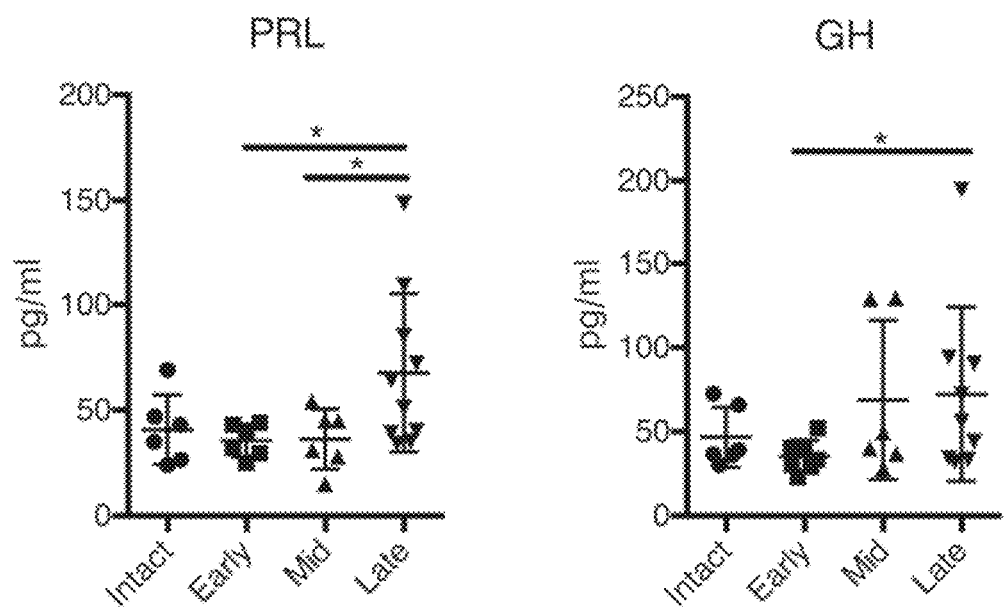
FIG. 6 is graphs showing the expression level of prolactin or growth hormone in the CSF in each progression stage of EAE pathology.

The results are shown in FIG. 6. It was observed that in the mid-stage EAE pathology, in the late-stage EAE pathology, the protein expression levels the protein expression levels of growth hormone increased; and of prolactin and growth hormone increased.

(7) Effects of Culturing in Co-Presence of Prolactin on Eomes Expression

Spleen-derived CD226$^+$CD4$^+$ T cells collected from each intact wild-type B6 mouse were cultured for 4 h or 8 h in the absence of prolactin or in the presence of each specific amount of prolactin. The Eomes expression levels in the respective cells after the culturing were measured by using a flow cytometer or a quantitative real-time PCR assay. As antibodies used at the detection were an anti-CD4 antibody (manufactured by Biolegend, Inc.) and an anti-Eomes antibody (manufactured by eBioscience, Inc.).

Figure 7:
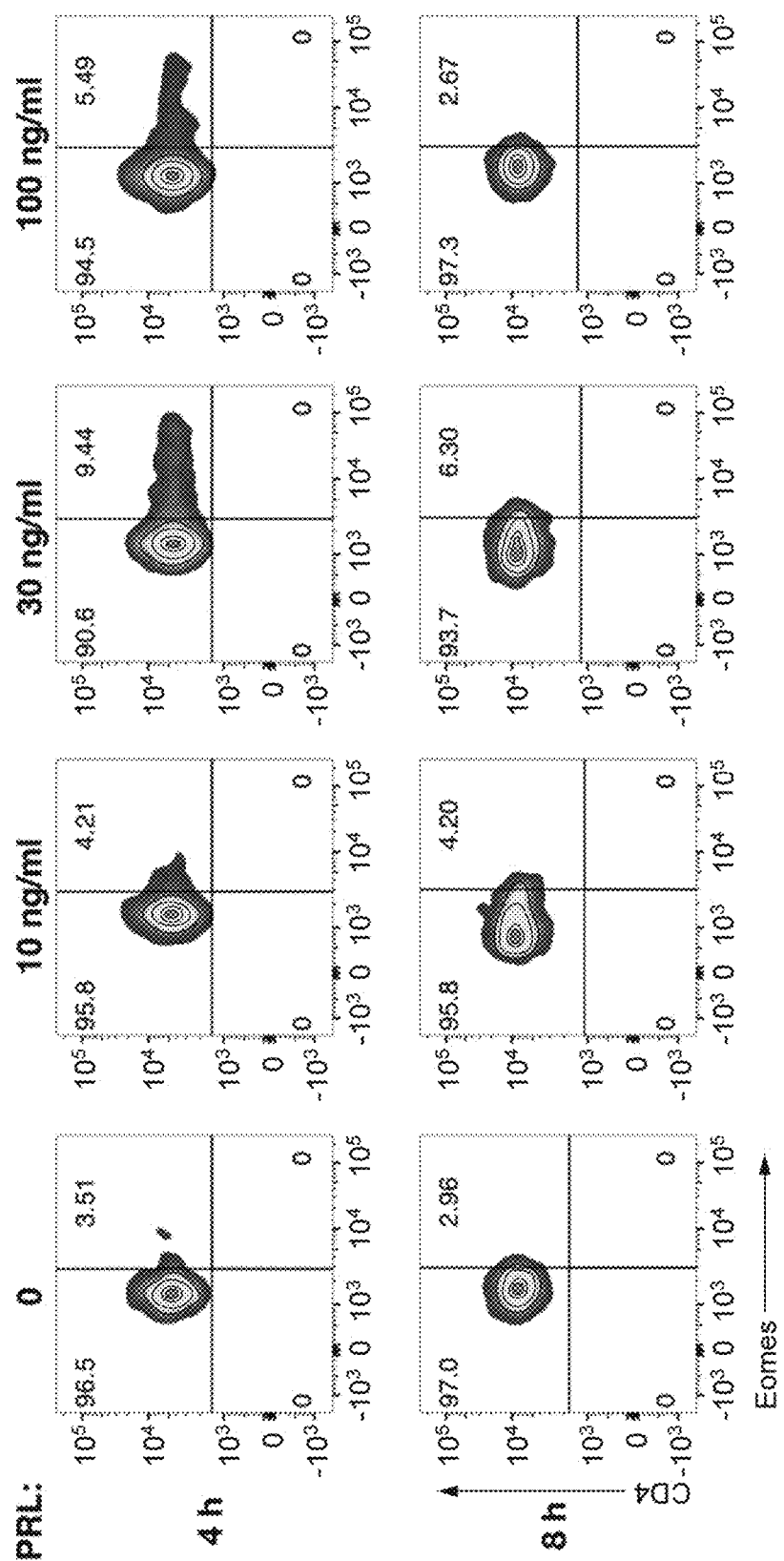
FIG. 7 is graphs showing the effects of culturing in the co-presence of prolactin on Eomes expression.
Figure 8A:
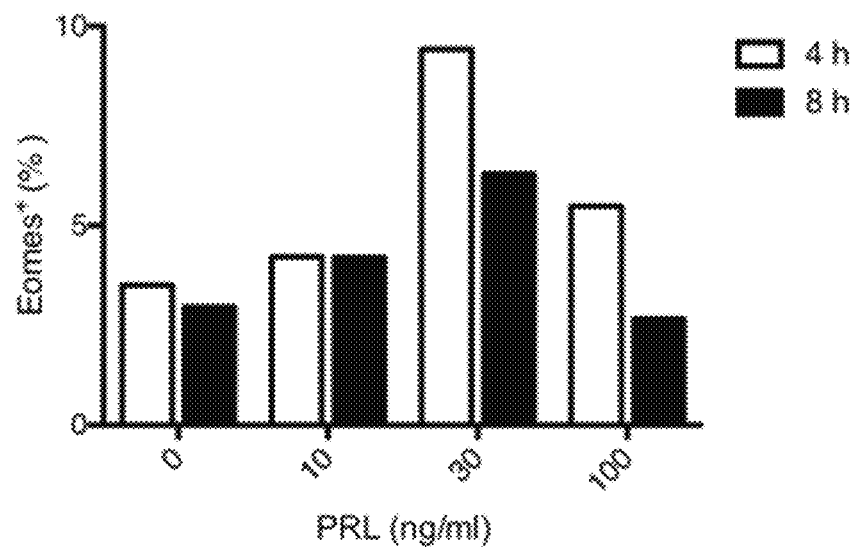
FIG. 8A provides a graph with the percentage of Eomes$^+$ cells on the basis of each flow cytogram shown in FIG. 7.
Figure 8B:
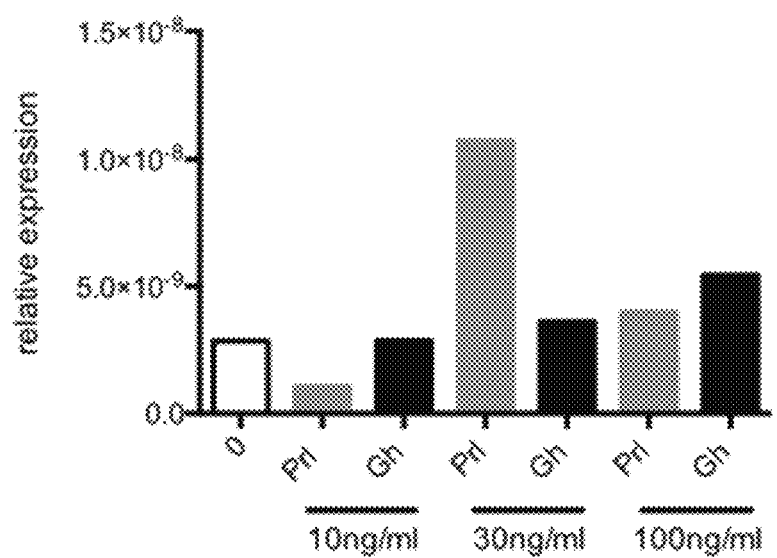
FIG. 8B shows the relative expression level of prolactin protein in the respective cells.

The results are shown in FIG. 7. It was observed that when cultured in the presence of prolactin at 30 or 100 ng/mL, the percentage of CD4$^+$Eomes$^+$ T cells increased markedly regardless of the culturing time. FIG. 8($a$) collectively provides, as a graph, each percentage of Eomes$^+$ cells on the basis of each flow cytogram shown in FIG. 7. FIG. 8($b$) shows, as a graph, the relative expression level of prolactin protein in the respective cells. In FIG. 8, It was also observed that when the cells were cultured in the presence of prolactin at 30 ng/mL, the gene expression levels of prolactin protein increased.

(8) Change in Gene Expression Levels of Each of Prolactin and Zbtb20 During Course of Progression of EAE Pathology In a similar manner to the above 1.(3), CD19$^+$ B cells or non-B/class II$^+$ cells were isolated over time from the CNS of each mouse with EAE. Then, the gene expression levels of each of prolactin and Zbtb20 were analyzed by a quantitative PCR assay. As primers for prolactin and Zbtb20 were used those in Mm_Prl_1_SG QuantiTect Primer Assay and Mm_Zbtb20_1_SG QuantiTect Primer Assay (both from QIAGEN Inc.), respectively.

Figure 9:
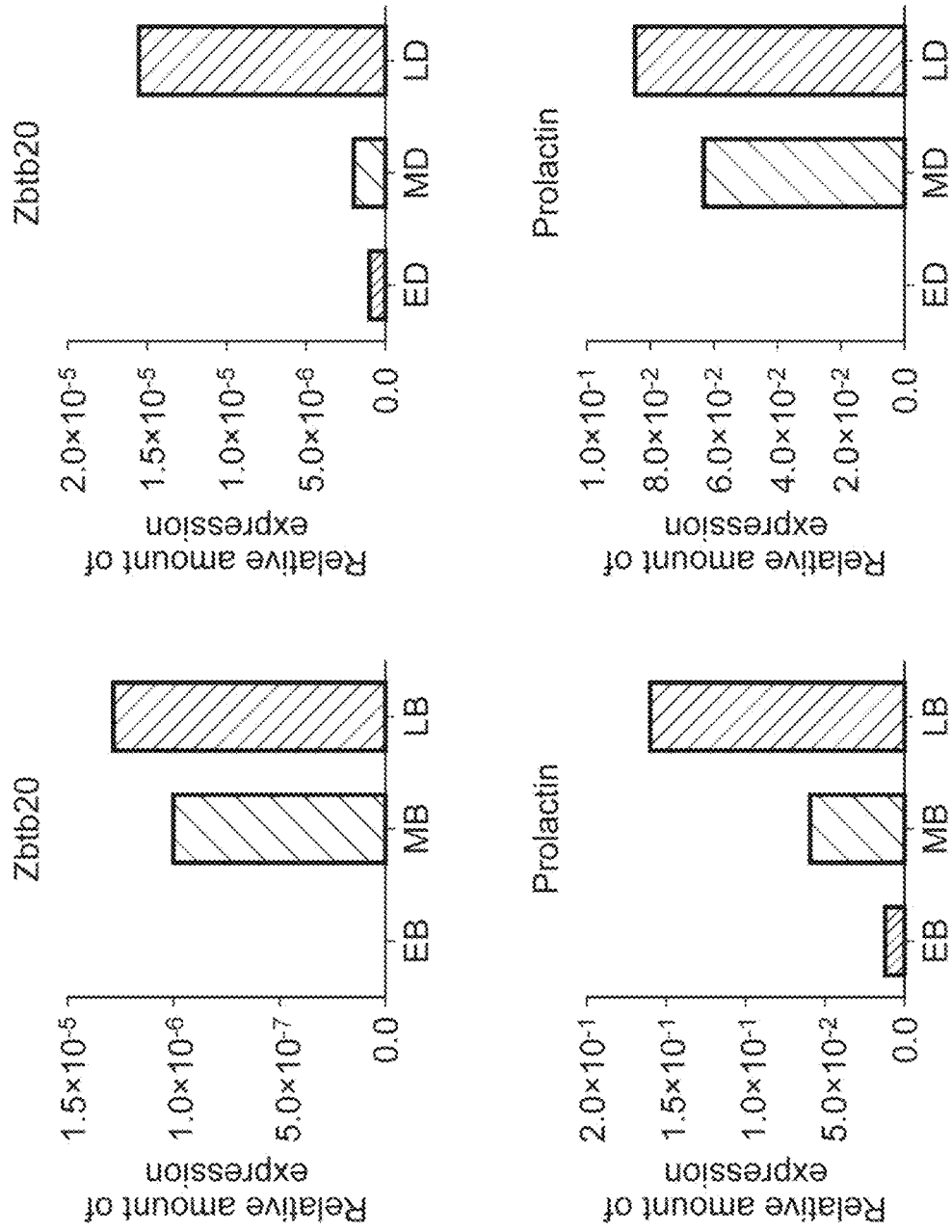
FIG. 9 is graphs showing the gene expression levels of each of prolactin and Zbtb20 in antigen-presenting cells infiltrated into the CNS of each NR4A2-deficient mouse in which monophasic EAE was induced.

The results are shown in FIG. 9. The "EB", "MB", "LB", "ED", "MD", and "LD" in FIG. 9 are each defined in the same manner as in FIG. 5. According to FIG. 9, it was observed that the gene expression levels of each of prolactin and Zbtb20 increased in the antigen-presenting cells derived from the CNS in the late-stage EAE conditions.

(9) Change in Protein Expression Levels of Each of Prolactin and Zbtb20 During Course of Progression of EAE Pathology From each C57BL/6 mouse (Control) and each NR4A2-deficient mouse (NR4A2c KO) in which monophasic EAE had been induced in a similar manner to the above 1.(2), the brain and the spinal cord were collected at day 9 after the induction (corresponding to the early-stage EAE pathology) and day 19 after the induction (corresponding to the late-stage EAE pathology). Then, a flow cytometer was used to separate CD19$^+$ B cells and non-B/class II$^+$ cells infiltrated into the CNS. Specifically, each tissue was cut into small pieces, which were then further dissociated at 37° C. for 40 min in RPMI 1640 medium (manufactured by Invitrogen, Inc.) containing 1.4 mg/mL collagenase H and 100 μg/mL DNase I (manufactured by Roche Inc.). The resulting tissue homogenate was made to pass through a 70-μm cell strainer (manufactured by GE Healthcare, Inc.), and was centrifuged on a Percoll discontinuous density gradient (37%/80%) to enrich leukocytes. Next, CD19$^+$ B cells or non-B/class II$^+$ cells infiltrated into the CNS were analyzed with a FACS CANTO II (manufactured by BD Cytometry Systems, Inc.). The flow cytometer was used to analyze a change in the expression level of Zbtb20 in the CD19$^+$ T cells or non-B/ class II⁺ cells separated. As an antibody used at the detection was an anti-Zbtb20 antibody (manufactured by BD Bioscience, Inc.).

Figure 11A:
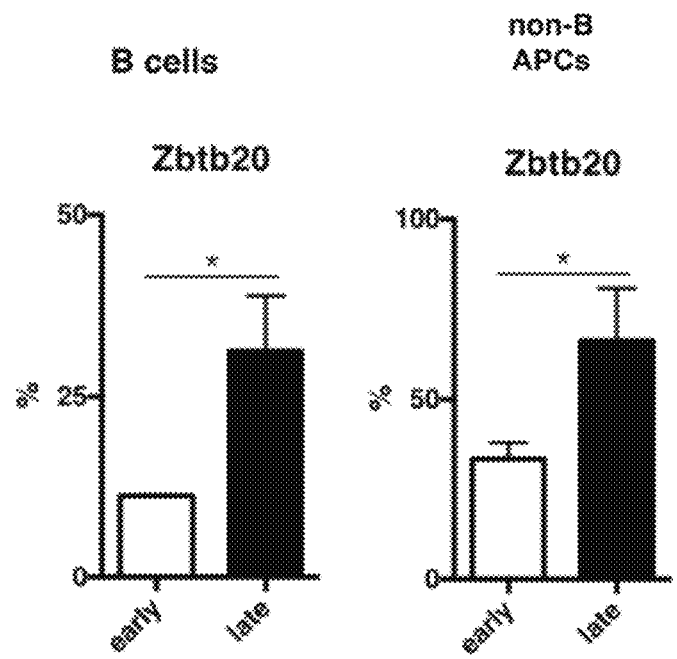
FIG. 11 is graphs showing Zbtb20 (FIG. 11A) or prolactin protein (FIG. 11B) expression in antigen-presenting cells infiltrated into the CNS of each NR4A2-deficient mouse in which monophasic EAE was induced.
Figure 11B:
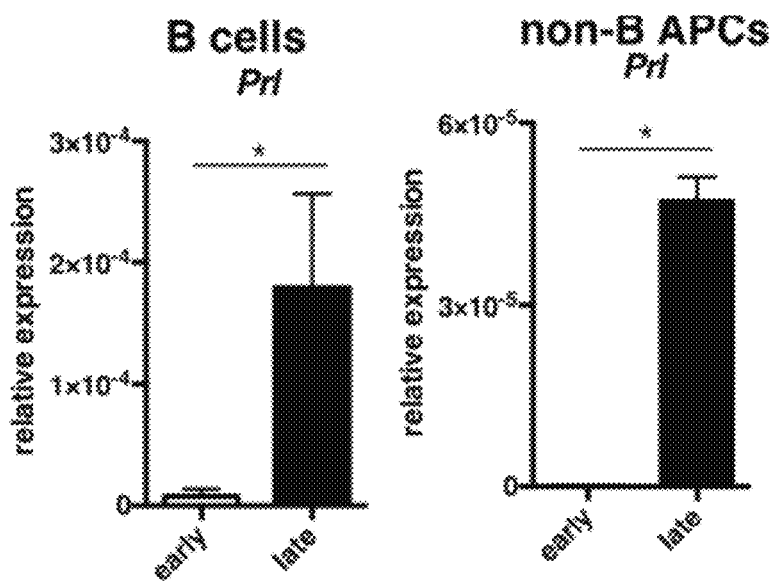

The results are shown in FIGS. 10 and 11. In FIG. 10, it was observed that the gene expression levels of Zbtb20 increased significantly in the late-stage EAE pathology. Meanwhile, FIG. 11(a) shows, as a graph, each percentage of Zbtb20⁺ cells; and it was observed that the Zbtb20 expression increased markedly in the late-stage EAE pathology. In addition, as shown in FIG. 11(b), the gene expression levels of prolactin gene (Prl) were measured in the B cells or the non-B antigen-presenting cells; and it was observed that the relative expression level of prolactin gene (Prl) increased markedly in the late-stage EAE pathology.

Figure 12A:
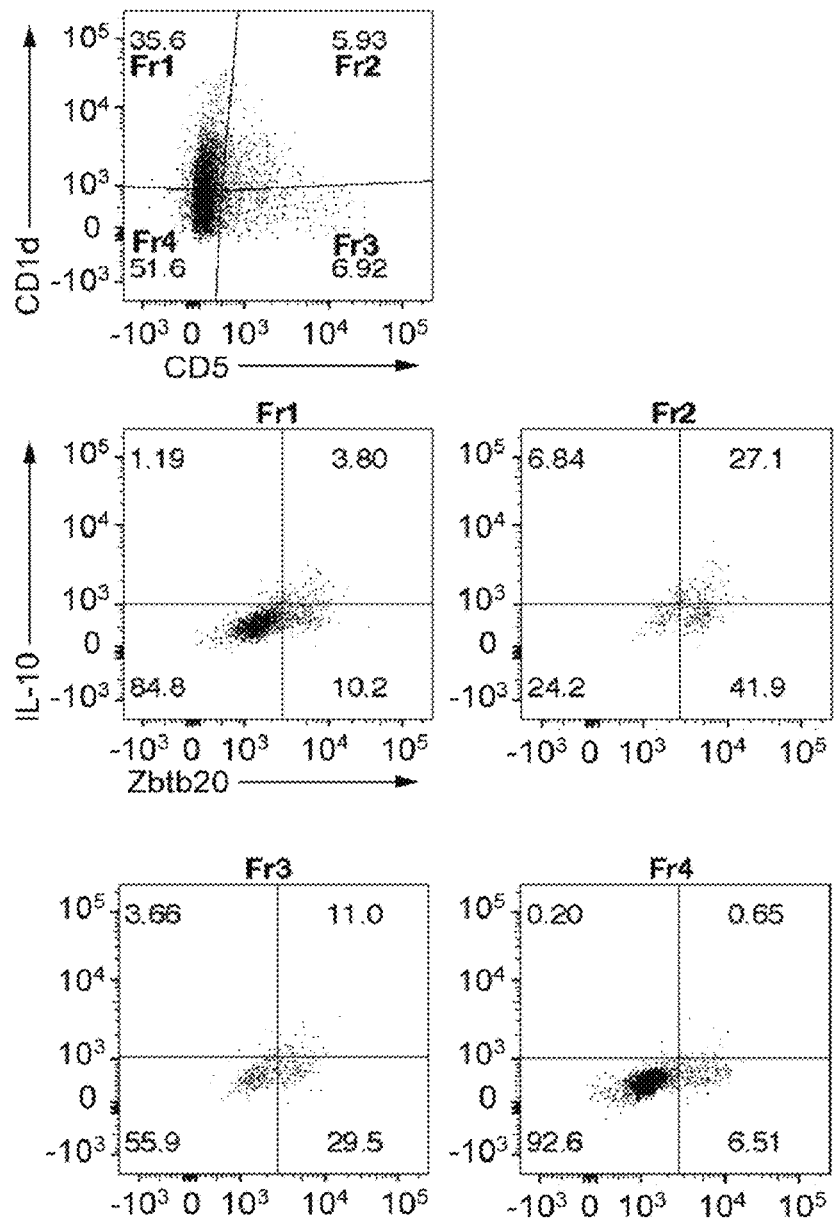
FIG. 12 is cytograms (FIG. 12A) and a graph (FIG. 12B) showing the IL-10 and Zbtb20 gene expression levels in B cells collected from the CNS of each mouse with the late-stage EAE pathology.
Figure 12B:
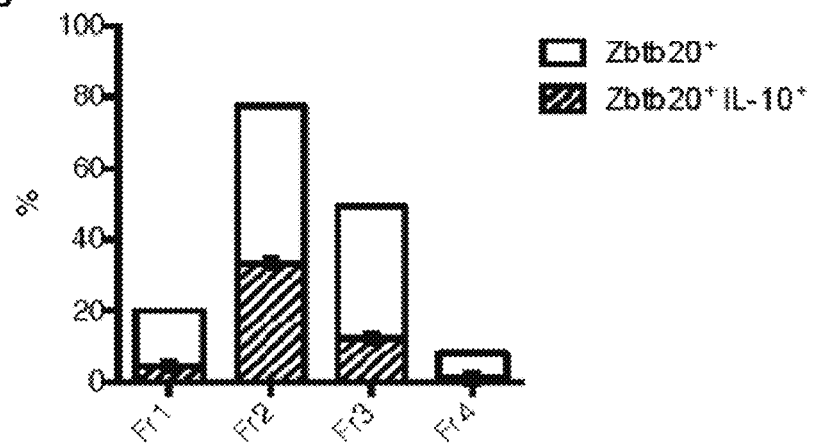

In addition, B cells collected from the CNS of each mouse with the late-stage EAE pathology were cultured for 6 h in the presence of 10 ng/mL lipopolysaccharide (LPS) and BD GolgiPlug. The cultured B cells were sorted, based on the staining conditions of CD1d and CD5 genes, into 4 different fractions (Fr1, Fr2, Fr3, and Fr4) as shown in FIG. 12(a). The IL-10 and Zbtb20 gene expression levels in each fraction were measured in FACS plots. The results are shown in FIG. 12(b).

Figure 13A:
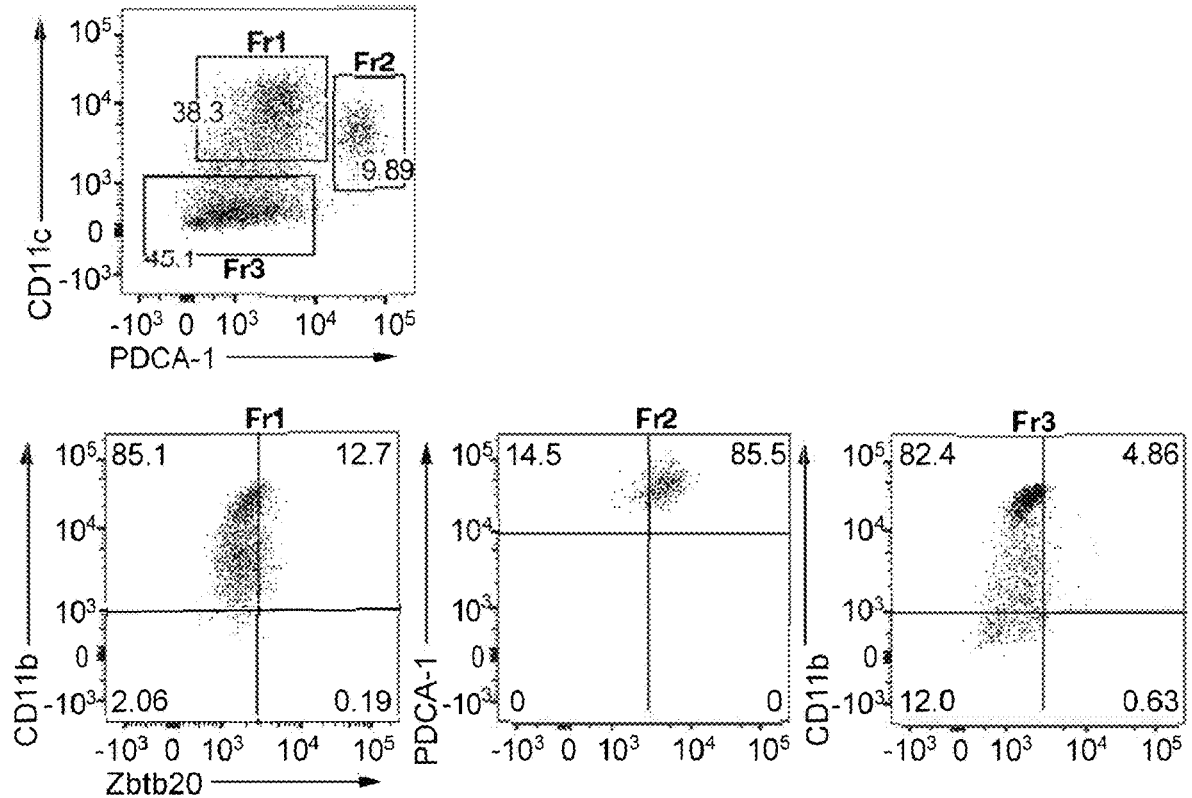
FIG. 13 is cytograms (FIG. 13A) and a graph (FIG. 13B) showing the Zbtb20 gene expression levels in non-B antigen-presenting cells collected from the CNS of each mouse with the late-stage EAE pathology.

Further, non-B antigen-presenting cells collected from the CNS of each mouse with the late-stage EAE pathology were stained and analyzed by FACS. The non-B antigen-presenting cells were sorted, based on the staining conditions of CD11c and PDCA-1 genes, into 3 different fractions (Fr1, Fr2, and Fr3) as shown in FIG. 13(a). The Zbtb20 gene expression levels in each fraction were measured in FACS plots. As antibodies used at the detection were an anti-CD11c antibody (manufactured by Biolegend, Inc.), an anti-PDCA-1 antibody (manufactured by eBioscience, Inc.), and an anti-zbtb20 antibody (manufactured by Becton Dickinson, Inc.).

Figure 13B:
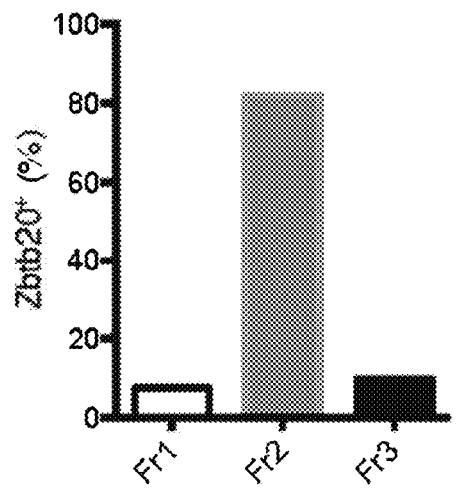

The results are shown in FIG. 13(a). In addition, FIG. 13(b) shows the percentage of Zbtb20⁺ cells in each fraction.

(10) Expression of Prolactin or Growth Hormone in Pituitary

Figure 14A:
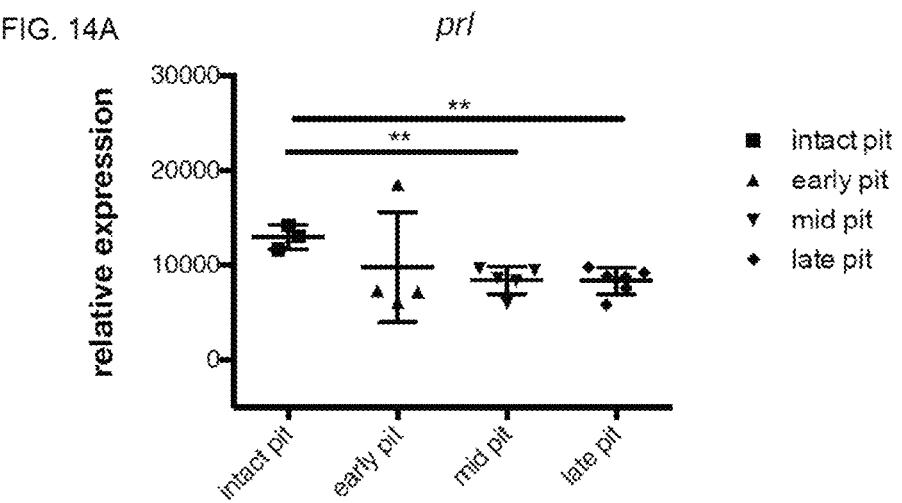
FIG. 14 is graphs showing the expression level of prolactin (FIGS. 14A, 14B, and 14C) or growth hormone (FIG. 14B) in the pituitary.

From each intact mouse or each mouse with the early-, mid-, or late-stage EAE pathology, the pituitary was excised, total RNA was isolated, and the expression levels of prolactin gene (Prl) were then measured by using a quantitative real-time PCR assay. The results are shown in FIG. 14(a).

Figure 14B:
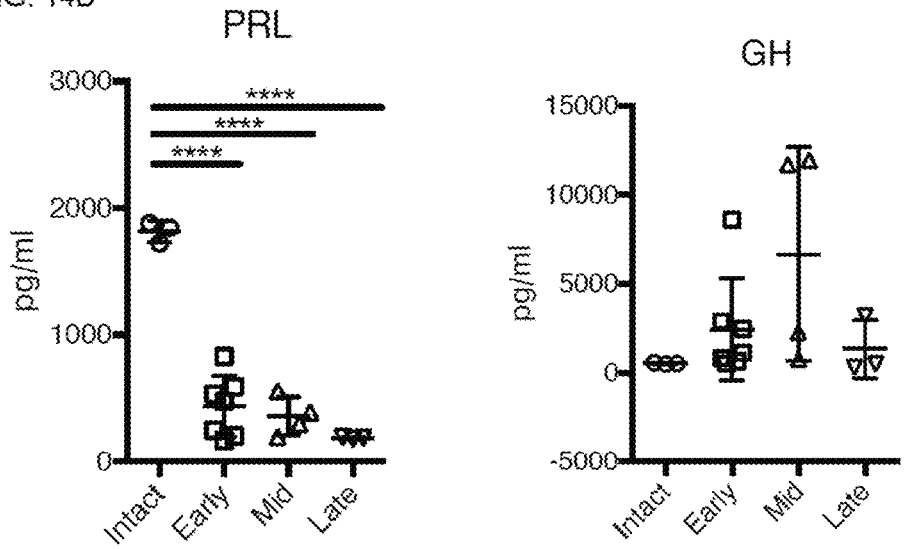

In addition, serum of each mouse was collected and a Luminex system was used to measure the protein levels of each of prolactin (PRL) and growth hormone (GH) in each serum. The results are shown in FIG. 14(b). In any of the progression stages of EAE pathology, it was observed that the serum prolactin (PRL) levels were markedly lower than those of each intact mouse.

Further, from the CNS of each intact mouse or each mouse with the early-, mid-, or late-stage EAE pathology, a FACS ARIA was used to purify CD19⁺ B cells, PDCA-1⁺CD11c⁺ plasma cell-like dendritic cells (pDCs), and CD45$^{int}$CD11b⁺ microglial cells. Then, the prolactin gene (Prl) and zbtb20 gene expression levels were measured by using a quantitative real-time PCR assay. As antibodies used at the detection were an anti-CD19 antibody (manufactured by Biolegend, Inc.), an anti-PDCA-1 antibody (manufactured by eBioscience, Inc.), an anti-CD45 antibody (manufactured by Biolegend, Inc.), an anti-CD11c antibody (manufactured by Biolegend, Inc.), and an anti-zbtb20 antibody (manufactured by Becton Dickinson, Inc.). To quantify Prl and GH, a Mouse pituitary magnetic bead panel (manufactured by Millipore, Inc.) was used.

Figure 14C:
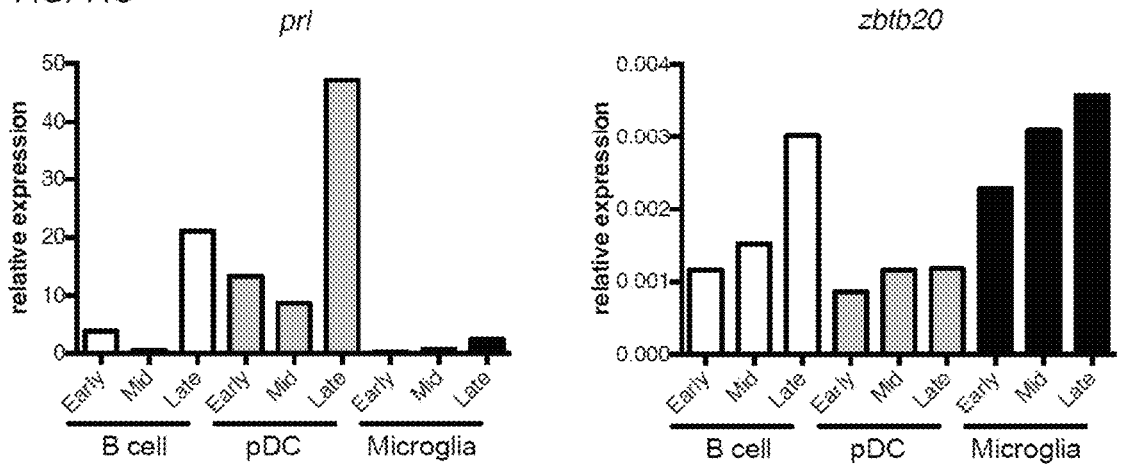

The results are shown in FIG. 14(c). It was observed that the expression levels of prolactin gene increased markedly in CD19⁺ B cells and PDCA-1⁺B220⁺pDCs in the late-stage EAE pathology. In addition, it was observed that the expression levels of zbtb20 gene increased in CD19⁺ B cells and CD45$^{int}$CD11b⁺ microglial cells as the EAE pathology progressed.

2. Change in Late-Stage EAE Pathology by Prolactin (1) Prolactin Addition and Enhanced Expression of Eomes Gene-1

Spleen-derived Th cells of each intact mouse were cultured for 8 h in the absence or presence of recombinant prolactin. After the culturing, total RNA was extracted from the Th cells. A first strand cDNA synthesis kit (manufactured by Takara Bio Inc.) was used to synthesize cDNA from the total RNA obtained. A Light Cycler instrument was used under conditions using a Light Cycler-Fast Start DNA Master SYBR Green I kit (manufactured by Roche Diagnostics, Inc.) or an ABI 7300 real-time PCR instrument was used under conditions using a Power SYBR Green Master mix (manufactured by Applied Biosystems, Inc.) to perform a quantitative real-time PCR assay by using commercially available primers (QuantiTect Primer Assay, QT01074332; manufactured by Qiagen, Inc.). The Eomes gene expression levels were corrected based on the expression level of a housekeeping gene GAPDH.

Figure 15:
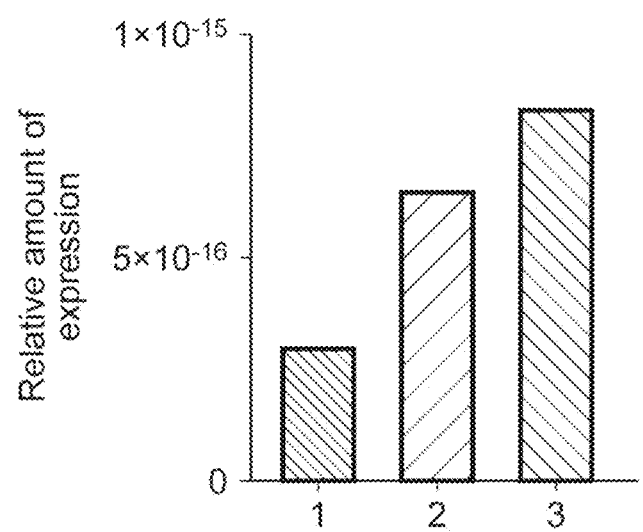
FIG. 15 is a graph showing the Eomes expression levels in spleen-derived Th cells cultured in the presence or absence of prolactin.

The results are shown in FIG. 15. In FIG. 15, a reference numeral "1" denotes the level obtained by culturing without addition of prolactin; a reference numeral "2" denotes the level obtained by culturing in the presence of prolactin at a low concentration; and a reference numeral "3" denotes the level obtained by culturing in the presence of prolactin at a high concentration. In FIG. 15, the ordinate represents the relative expression level of Eomes relative to that of a housekeeping gene (β2-microglobulin); and the Eomes expression level increased in a prolactin concentration-dependent fashion.

(2) Prolactin Addition and Enhanced Expression of Eomes Protein-2

Spleen-derived CD226⁺ Th cells were cultured for 8 h or 48 h in the absence or presence of prolactin. After the culturing, the CD226⁺ Th cells were stained with an anti-CD226 antibody and an anti-Eomes antibody, and a FACS CANTO II (manufactured by BD Cytometry Systems, Inc.) was used to analyze CD226⁺Eomes⁺ T cells, CD226⁺Eomes⁻ T cells, and CD226⁻ T cells. As the antibodies used during the analysis were an anti-CD226 antibody (manufactured by Biolegend, Inc.) and an anti-Eomes antibody (manufactured by Biolegend, Inc.).

Figure 16:
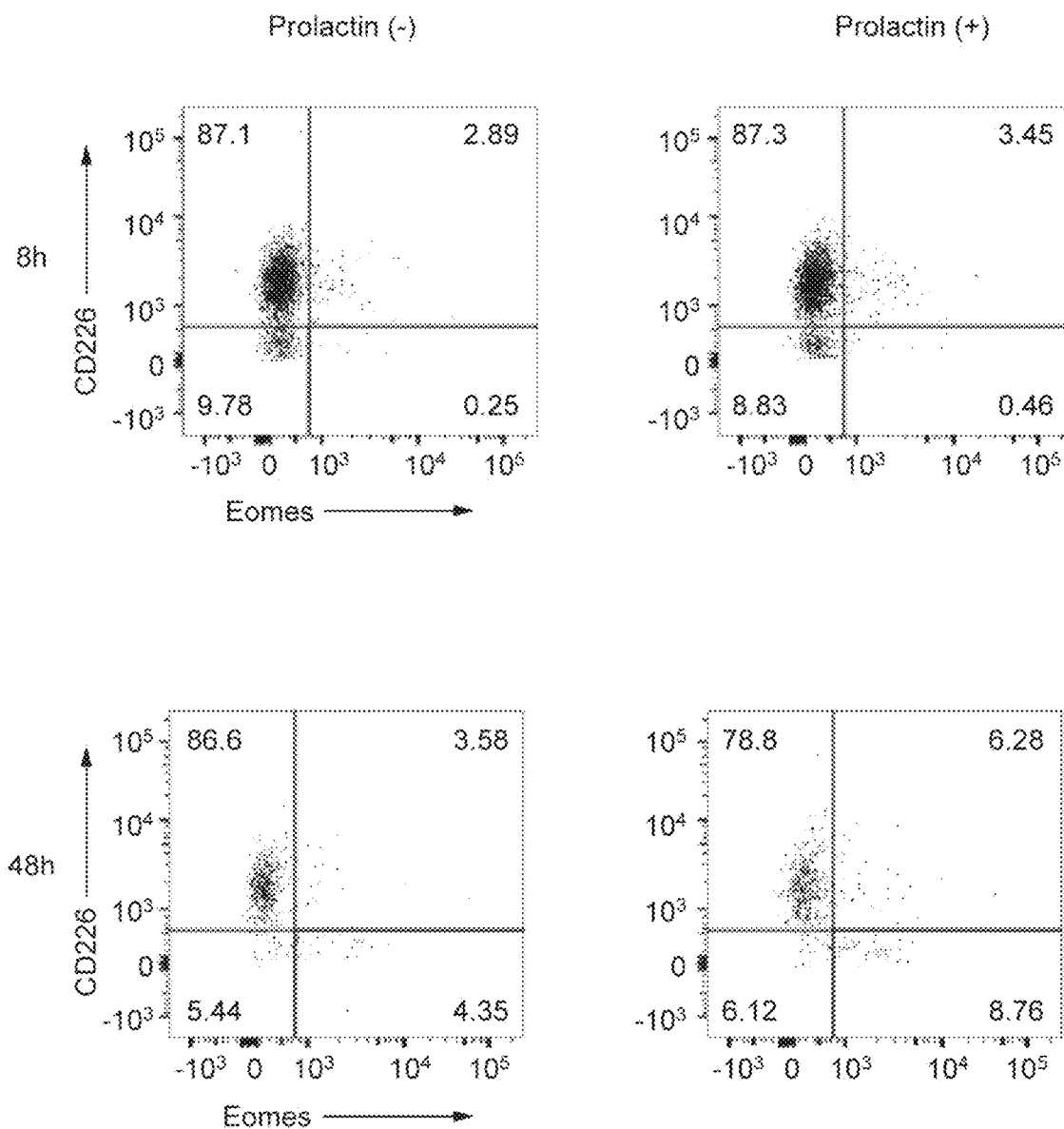
FIG. 16 is cytograms showing Eomes expression in spleen-derived CD226$^+$ Th cells cultured in the presence or absence of prolactin.

The results are shown in FIG. 16. The Eomes expression levels in the cells after cultured for 48 h in the presence of prolactin increased more markedly than in the cells after cultured in the absence of prolactin.

(3) Suppression of Late-Stage EAE Pathology by D2 Receptor Agonist

Into each control mouse (Control) or each CD4-Cre/NR4A2$^{fl/fl}$ if mouse in which monophasic EAE had been induced in a similar manner to the above 1.(2), bromocriptine was intraperitoneally injected every other day from day 4 after the induction. After the injection, the EAE pathology of each mouse was daily evaluated in accordance with the EAE criteria as indicated below.

<EAE Criteria>
0: No clinical symptoms;
1: partial tail paralysis;
2: limp tail;
3: partial hindlimb paralysis;

4: complete hindlimb paralysis

5: hindlimb and forelimb paralysis.

Figure 17:
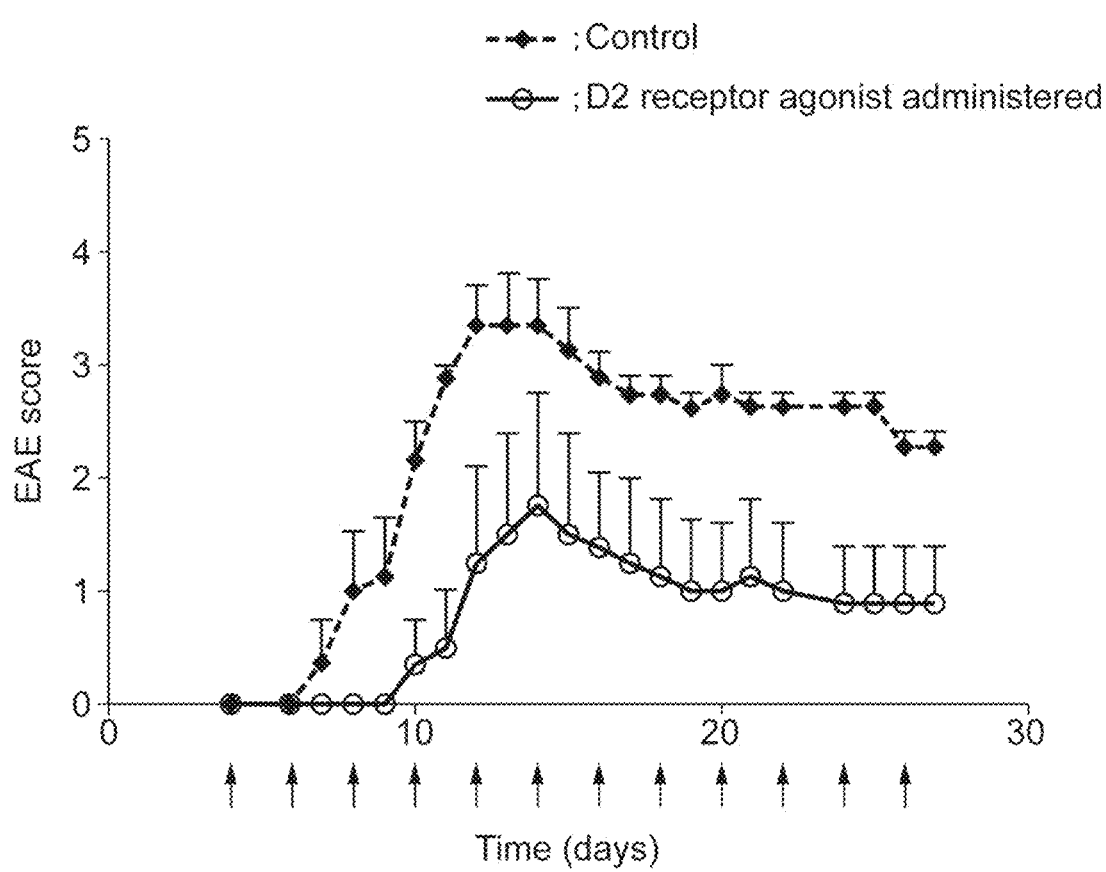
FIG. 17 is a graph showing the EAE scores when bromocriptine was administered to each NR4A2-deficient mouse in which monophasic EAE had been induced.

The results are shown in FIG. 17. Each arrow in FIG. 17 denotes the day when bromocriptine was administered. The bromocriptine dosing caused the late-stage EAE pathology to be suppressed significantly.

(4) Suppression of Expression of Eomes Protein by D2 Receptor Agonist (Bromocriptine) Dosing–1

Regarding each CD4-Cre/NR4A2$^{fl/fl}$ mouse in which monophasic EAE had been induced in a similar manner to the above 1.(2), the brain and the spinal cord were collected from each non-injected mouse and each mouse into which bromocriptine was intravenously injected every other day from day 4 after the induction. Then, a flow cytometer was used to separate Th cells infiltrated into the CNS. Specifically, each tissue was cut into small pieces, which were then further dissociated at 37° C. for 40 min in RPMI 1640 medium (manufactured by Invitrogen, Inc.) containing 1.4 mg/mL collagenase H and 100 μg/mL DNase I (manufactured by Roche Inc.). The resulting tissue homogenate was made to pass through a 70-μm cell strainer (manufactured by GE Healthcare, Inc.), and was centrifuged on a Percoll discontinuous density gradient (37%/80%) to enrich leukocytes. Next, Th cells infiltrated into the CNS were sorted by FACS using a FACS ARIA II (manufactured by BD Cytometry Systems, Inc.). Then, a flow cytometer was used to analyze a change in the expression level of each of Eomes and CD4 in the Th cells recovered. As antibodies used at the sorting were an anti-CD4 antibody (manufactured by Biolegend, Inc.) and an anti-Eomes antibody (manufactured by eBioscience, Inc.).

Figure 18:
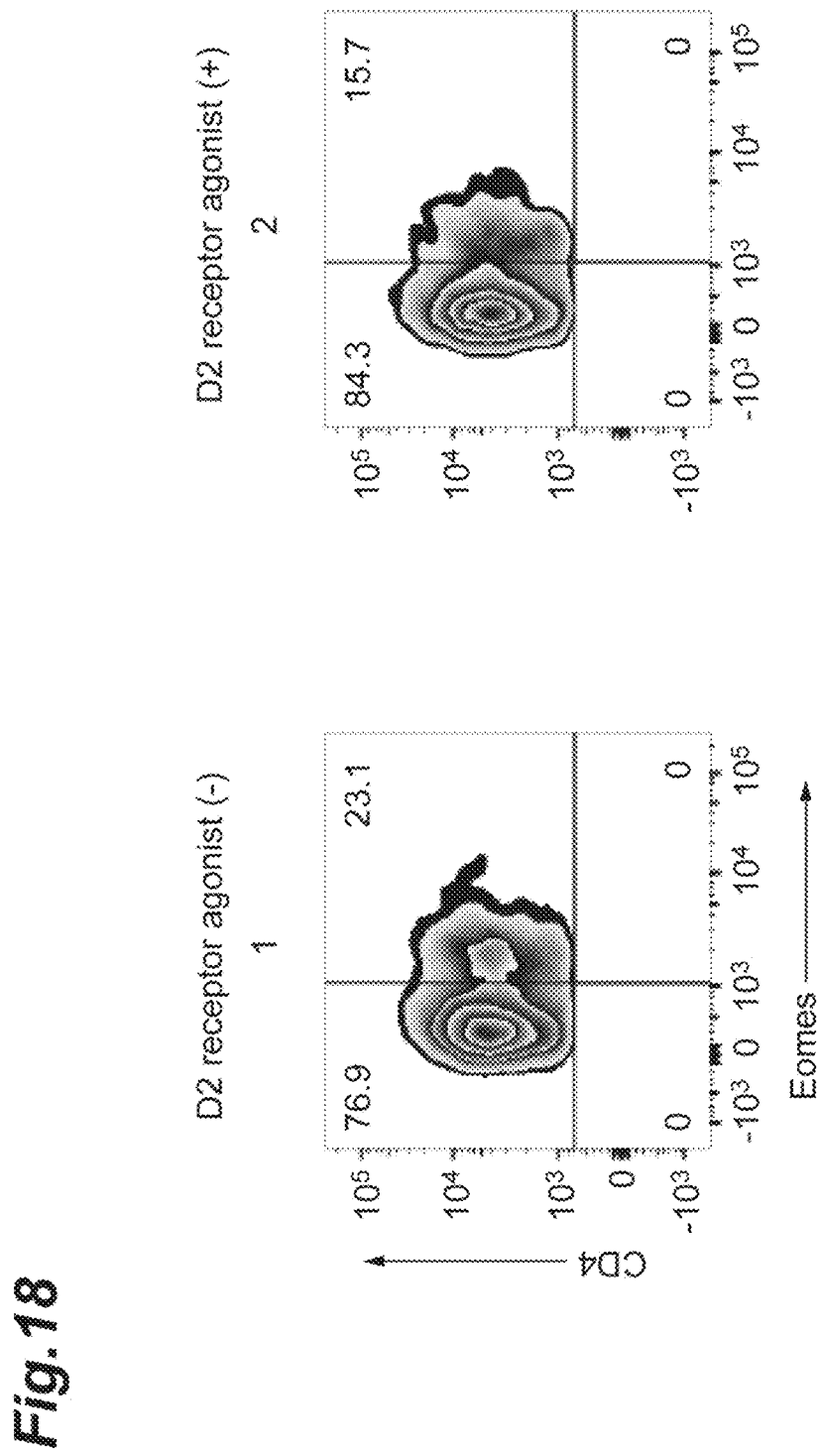
FIG. 18 is graphs showing Eomes expression in Th cells infiltrated into the CNS after bromocriptine was administered to each NR4A2-deficient mouse in which monophasic EAE had been induced.
Figure 19:
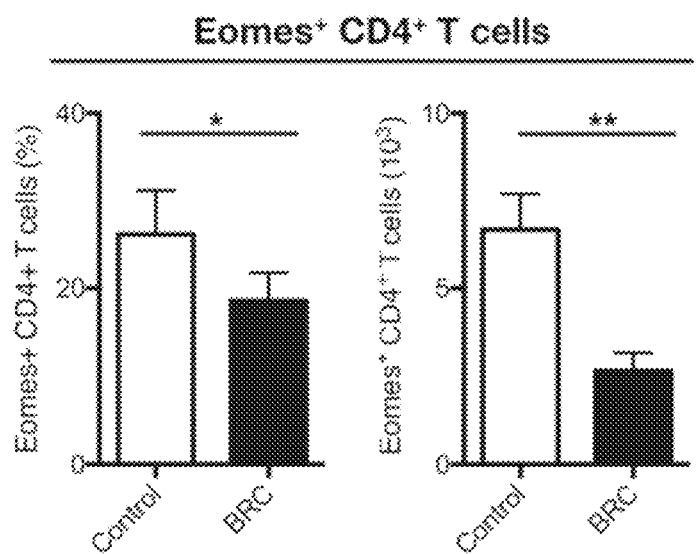
FIG. 19 is a graph showing the percentage of Eomes$^+$ CD4$^+$ T cells after bromocriptine dosing.

The results are shown in FIGS. 18 and 19. As shown in FIG. 18, the bromocriptine dosing caused the gene expression levels of Eomes protein in the CNS-infiltrated Th cells to be suppressed significantly. FIG. 19 is graphs showing changes in the percentage and the actual number of Eomes CD4$^+$ T cells.

(5) Suppression of Expression of Eomes Gene by D2 Receptor Agonist (Bromocriptine) Dosing–2

Regarding each CD4-Cre/NR4A2$^{fl/fl}$ mouse in which monophasic EAE had been induced in a similar manner to the above 1.(3), the brain and the spinal cord were collected, at day 27 after the induction, from each non-injected mouse and each mouse into which bromocriptine was intravenously injected, every other day from day 4 after the induction. Next, CD19$^+$ B cells or non-B/class II$^+$ cells infiltrated into the CNS were sorted by FACS using a FACS ARIA II (manufactured by BD Cytometry Systems, Inc.). The respective sorted CD19$^+$ B cells or non-B/class II$^+$ cells were co-cultured with spleen-derived CD4$^+$ Th cells for 8 h. After the culturing, a flow cytometer was used to analyze a change in the expression level of each of Eomes and CD107a in and on the Th cells recovered. As antibodies used at the detection were an anti-Eomes antibody (manufactured by eBioscience, Inc.) and an anti-CD107a antibody (manufactured by Biolegend, Inc.).

Figure 20:
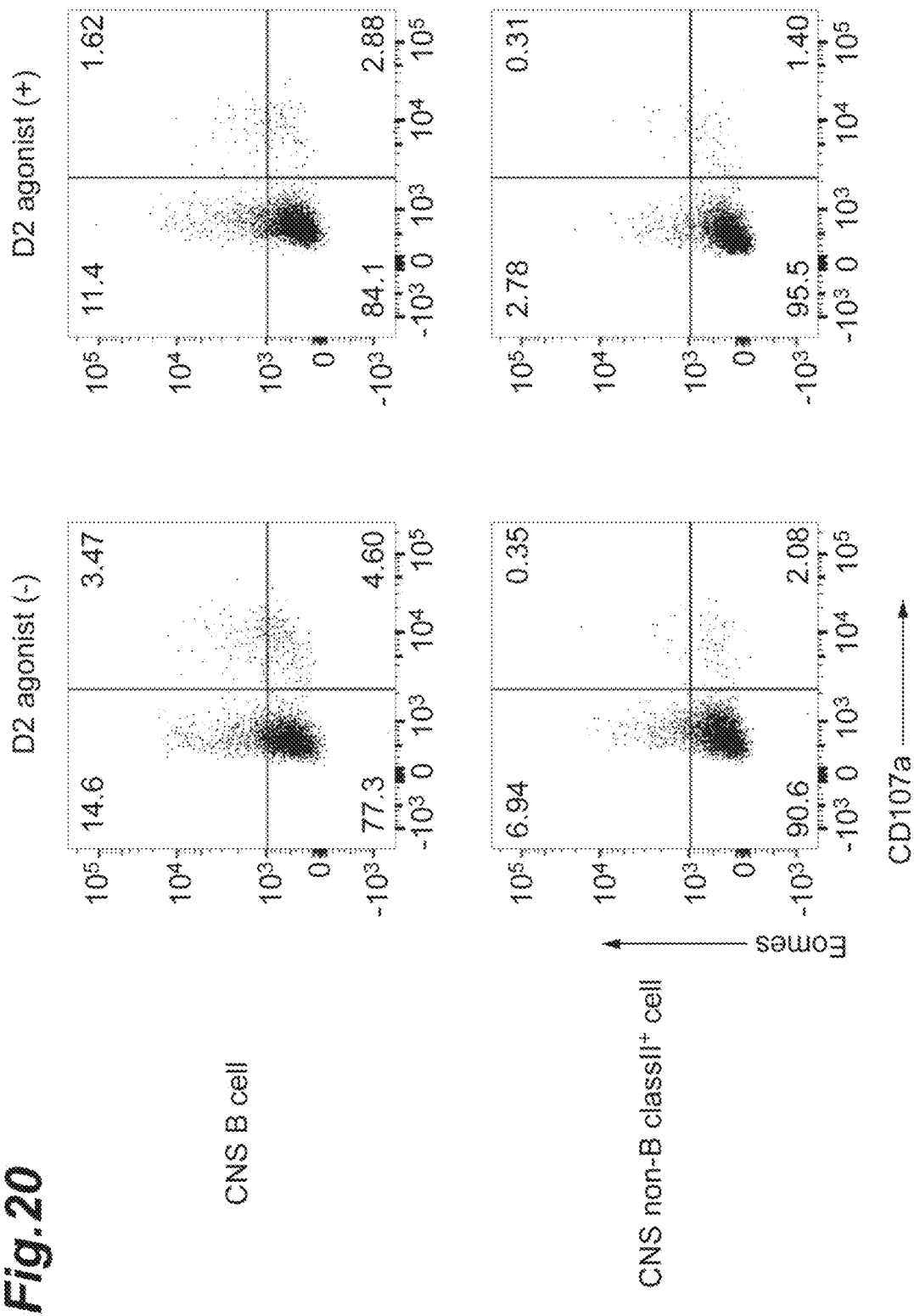
FIG. 20 is cytograms showing expression of CD107a and Eomes in Th cells infiltrated into the CNS when bromocriptine was administered to each NR4A2-deficient mouse in which monophasic EAE had been induced.

The results are shown in FIG. 20. According to FIG. 20, the bromocriptine dosing significantly suppressed the abilities of the CNS-derived antigen-presenting cells to induce CD107a expression and Eomes protein expression on and in the Th cells.

(6) Expression of Eomes Gene and CD107a Gene by D2 Receptor Agonist (Bromocriptine) Dosing Into each CD4-Cre/NR4A2$^{fl/fl}$ mouse in which monophasic EAE had been induced in a similar manner to the above 1.(3), bromocriptine or a placebo (DMSO and PBS) was intraperitoneally injected every other day from day 4 after the induction.

Next, the brain and the spinal cord were collected at day 32 after the induction; and CD19$^+$ B cells or CD19$^-$CD45$^{hi}$ non-B/class II$^+$ antigen-presenting cells infiltrated into the CNS were sorted by FACS using a FACS ARIA II (manufactured by BD Cytometry Systems, Inc.). The sorted cells were co-cultured, in the presence of an FITC-conjugated anti-CD107a antibody, with CD4$^+$ T cells sorted by FACS from the spleen derived from each intact mouse of similar genetic strain. The respective cells were co-cultured for 8 h, stained, and analyzed regarding the Eomes expression. As antibodies used at the detection were an anti-CD4 antibody (manufactured by Biolegend, Inc.), an anti-Eomes antibody (manufactured by eBioscience, Inc.), an anti-CD45 antibody (manufactured by Biolegend, Inc.), and an FITC-conjugated CD107a antibody (manufactured by Biolegend, Inc.).

Figure 21A:
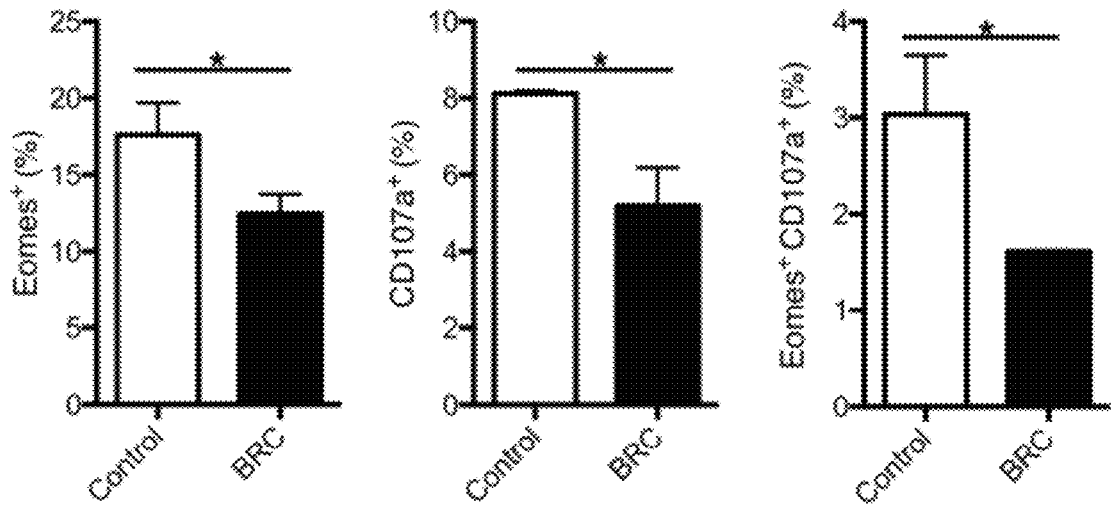
FIG. 21A is graphs showing the percentages of Eomes$^+$ CD4$^+$ B cells and the percentages of CD107a$^+$CD4$^+$ B cells after bromocriptine dosing.
Figure 21B:
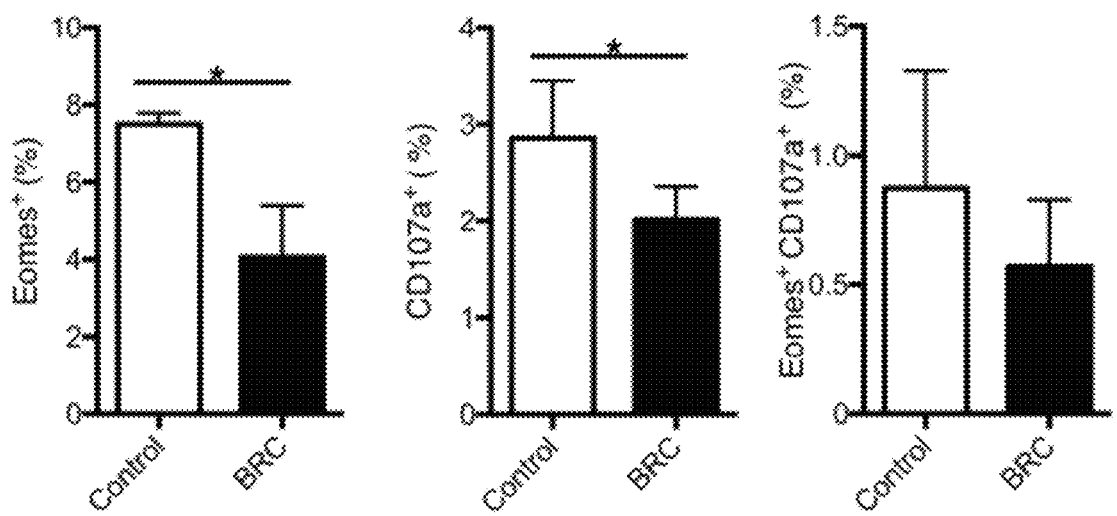
FIG. 21B is graphs showing the percentages of Eomes$^+$CD4$^+$ T cells and the percentages of CD107a$^+$CD4$^+$ T cells after bromocriptine dosing.

The results are shown in FIG. 21. It was observed that the Eomes gene and CD107a gene expression levels on the cell surface of the co-cultured CD4$^+$ T cells even when co-cultured with any of the CD19$^+$ B cells and CD19$^-$CD45$^{hi}$ non-B/class II$^+$ antigen-presenting cells decreased by the bromocriptine dosing.

(7) Suppression of Expression of Eomes Gene by D2 Receptor Agonist (Dopamine) Dosing CD19$^+$ B cells or CD19$^-$CD45$^{hi}$ non-B/class II$^+$ antigen-presenting cells were purified from each mouse with the late-stage EAE pathology by sorting by FACS. The respective purified cells were cultured for 24, 48, or 96 h in the absence of dopamine or in the presence of a specific amount of dopamine. Next, the cultured cells were recovered and the prolactin gene (Prl) and Zbtb20 gene expression levels were analyzed by using a quantitative real-time PCR assay.

Figure 22A:
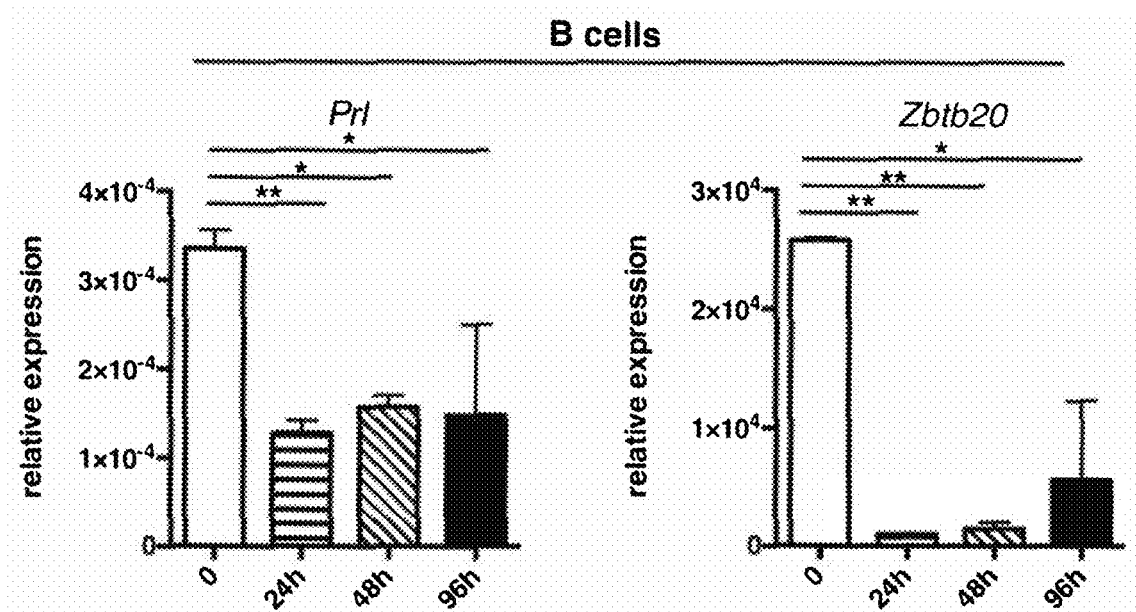
FIG. 22 is graphs showing Eomes gene expression after dopamine dosing in B cells (FIG. 22A) and T cells (FIG. 22B).
Figure 22B:
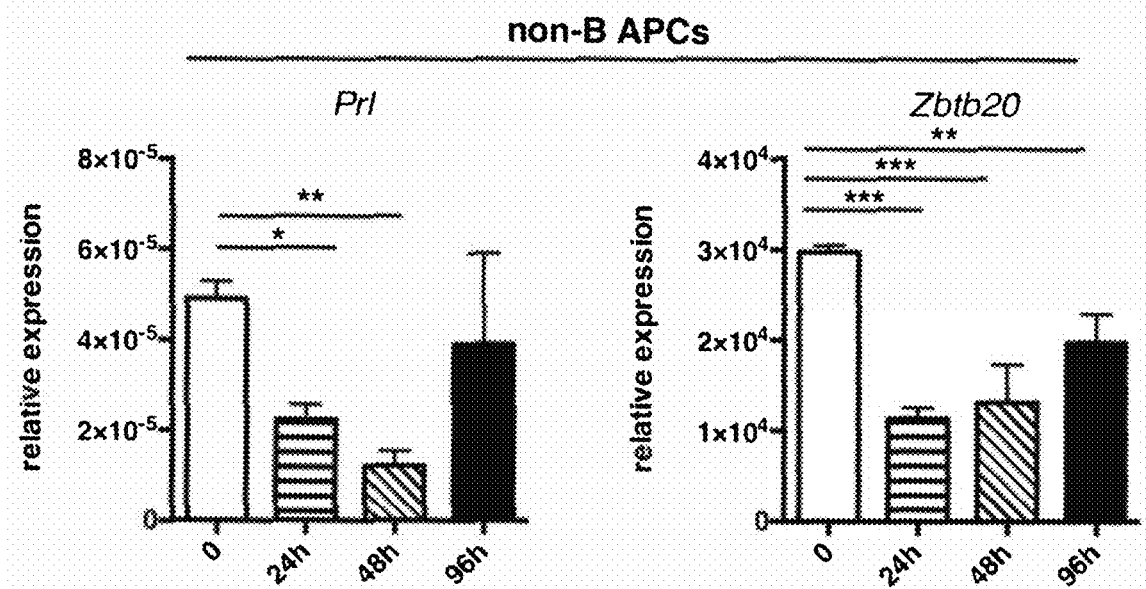

The results are shown in FIG. 22. FIG. 22(a) shows the gene expression levels in CD19$^+$ B cells; and FIG. 22(b) shows the gene expression levels in CD19$^-$CD45$^{hi}$ non-B class II$^+$ cells. It was observed that in either case, the prolactin and Zbtb20 gene expression levels decreased markedly after culturing in the co-presence of dopamine.

(8) Suppression of Expression of Eomes Gene by Dopamine Precursor Substance (L-Dopa) Dosing Into each CD4-Cre/NR4A2$^{fl/fl}$ mouse in which monophasic EAE had been induced in a similar manner to the above 1.(3), L-dopa or a placebo (DMSO and PBS) was intraperitoneally injected every other day from day 4 after the induction.

Figure 23:
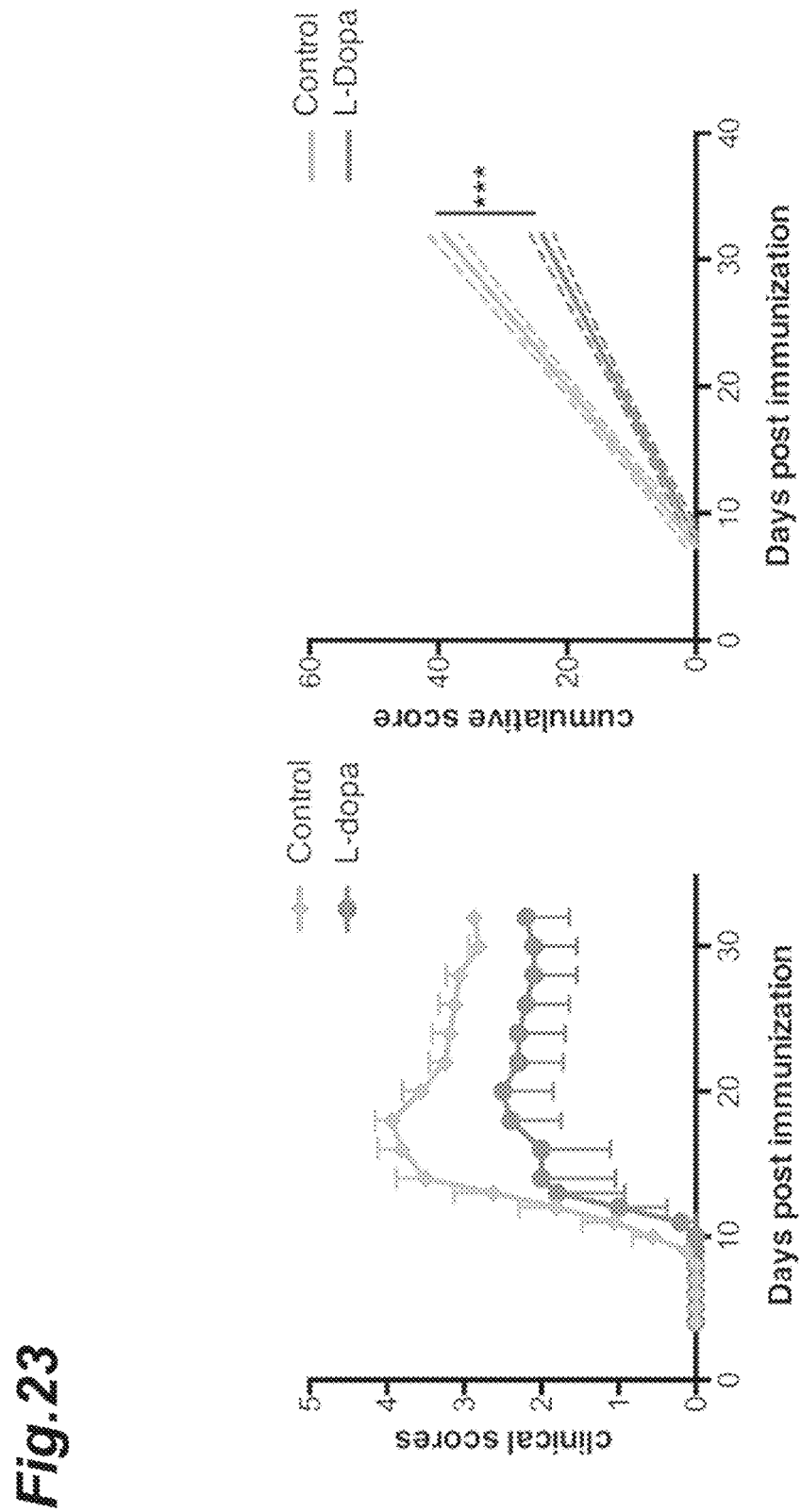
FIG. 23 is graphs showing the clinical scores in each EAE pathology mouse after L-dopa dosing.

The EAE scores of each mouse are shown in FIG. 23. It was observed that repeated dosing of L-dopa caused the EAE scores to improve markedly. In the right graph of FIG. 23, the dashed lines each indicate 95% confidence interval. In comparison with the cumulative EAE scores, an improvement in the EAE scores by the repeated dosing of L-dopa was confirmed.

Next, the brain and the spinal cord were collected from each mouse at day 32 after the induction; and CD4$^+$ T cells, CD19$^+$ B cells, or CD19$^-$CD45$^{hi}$ non-B/class II$^+$ antigen-presenting cells infiltrated into the CNS were sorted by FACS using a FACS ARIA II (manufactured by BD Cytometry Systems, Inc.). The respective sorted cells were stained and analyzed regarding the Eomes and Zbtb20 gene expressions. As antibodies used at the detection were an anti-CD4 antibody (manufactured by Biolegend, Inc.), an anti-Eomes antibody (manufactured by eBioscience, Inc.), an anti-CD19 antibody (manufactured by Biolegend, Inc.), and an anti-Zbtb20 antibody (manufactured by Becton Dickinson, Inc.).

Figure 24A:
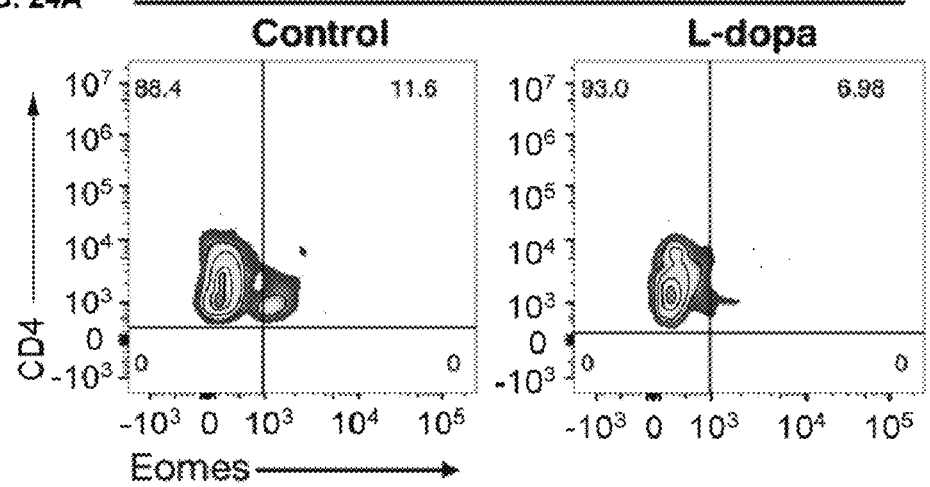
FIG. 24 is graphs showing expression of Eomes protein or Zbtb20 protein after dopamine dosing in CD4+ T cells (FIG. 24A), B cells (FIG. 24B), and non-B antigen presenting cells (FIG. 24C).
Figure 24B:
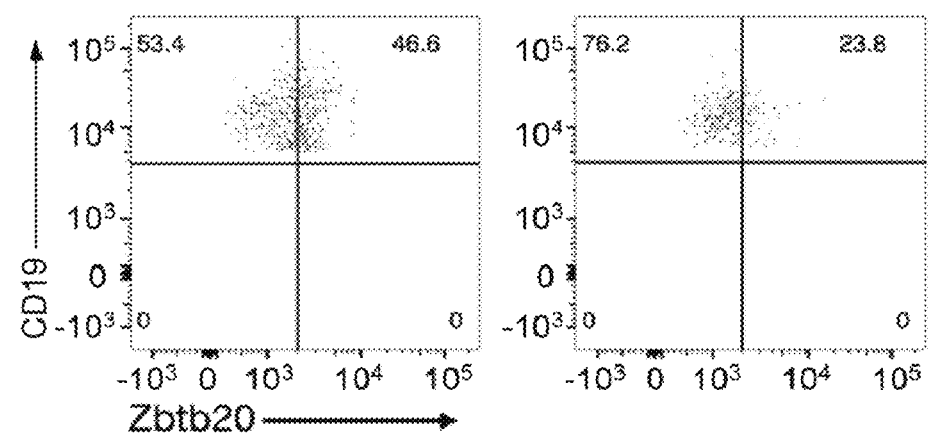
Figure 24C:
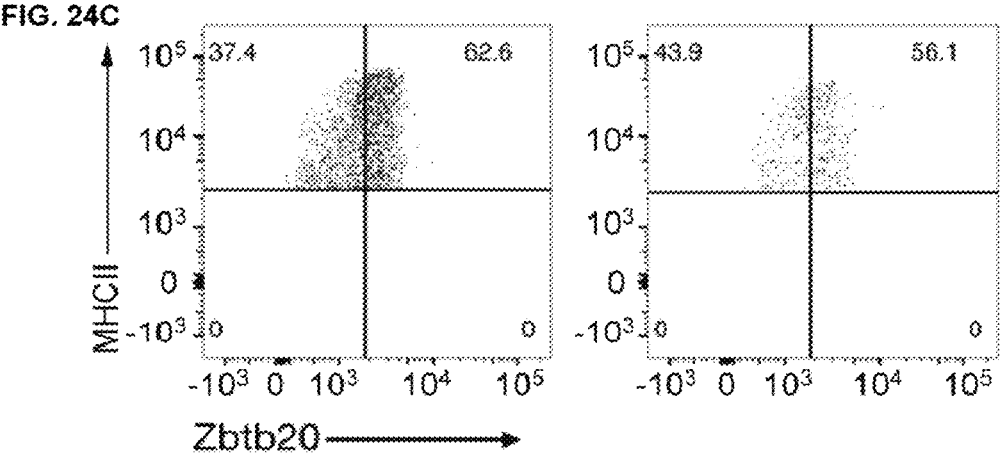

The results are shown in FIG. 24. As shown in FIG. 24(a), it was observed that the repeated dosing of L-dopa caused the percentage of CD4$^+$Eomes$^+$ T cells to decrease markedly in the CD4$^+$ T cells. In addition, as shown in FIGS. 24(b)

and (c), it was observed that the repeated dosing of L-dopa caused the percentage of Zbtb20⁺ cells to decrease in the CD19⁺ B cells and the CD19⁻CD45$^{hi}$ non-B/class II⁺ antigen-presenting cells.

Next, CD19⁺ B cells and CD19⁻CD45$^{hi}$ non-B/class II⁺ antigen-presenting cells were separated from the CNS or the spleen of each L-dopa-administered mouse or each intact mouse; and the expression levels of prolactin gene (Prl) in these types of cells were analyzed by using a quantitative real-time PCR assay. As antibodies used at the detection were an anti-CD19 antibody (manufactured by Biolegend, Inc.) and an anti-CD45 antibody (manufactured by Biolegend, Inc.).

Figure 25:
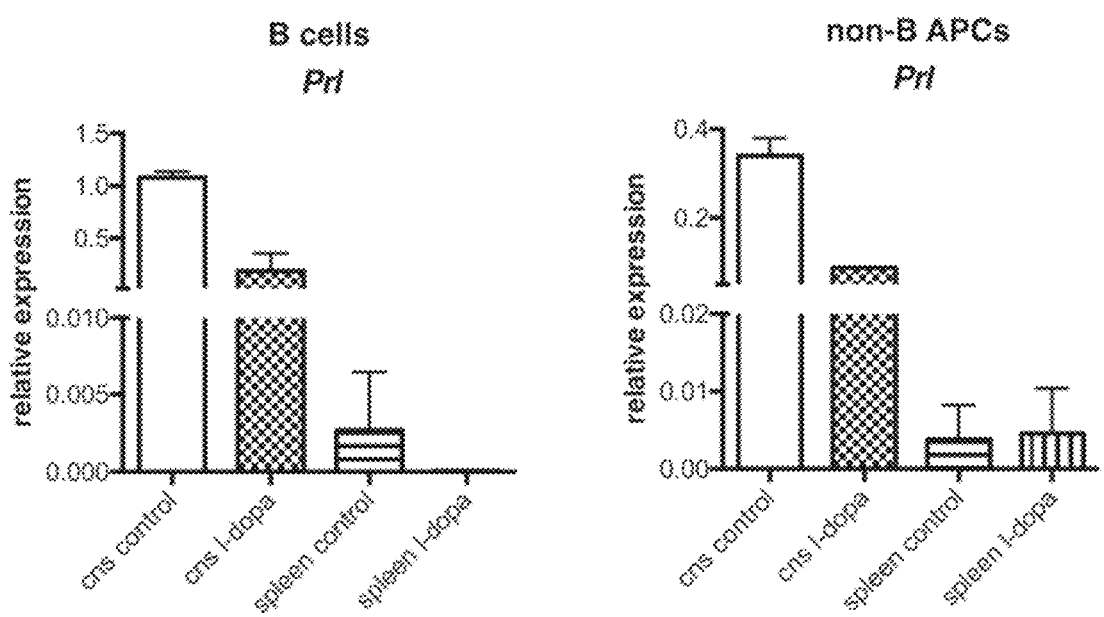
FIG. 25 is graphs showing the prolactin gene expression levels after L-dopa dosing.

The results are shown in FIG. 25. It was observed that the expression levels of prolactin gene were markedly high in the CNS-derived B cells and non-B/class II⁺ antigen-presenting cells; and the repeated dosing of L-dopa caused the expression levels to decrease.

3. Suppression of Expression of Eomes Gene by Anti-CX3CR1 Antibody Dosing

An anti-CX3CR1 antibody (manufactured by Biolegend, Inc.) or an isotype thereof (manufactured by Biolegend, Inc.) was administered to each NR4A2-deficient mouse, in which monophasic EAE had been induced in a similar manner to the above 1.(3), at day 10 after the induction. Then, the EAE pathology of each mouse was daily evaluated in accordance with the above-described EAE criteria.

Figure 26:
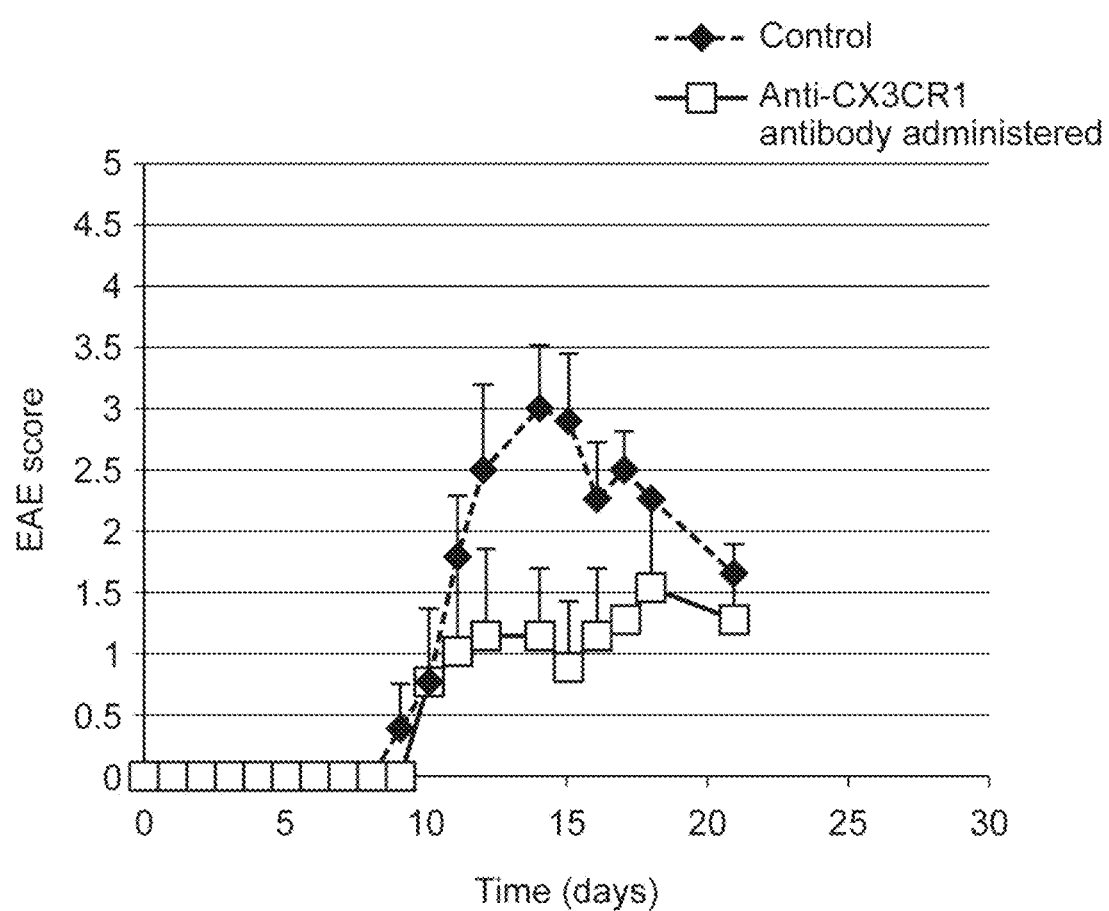
FIG. 26 is a graph showing the EAE scores when an anti-CX3CR1 antibody was administered to each NR4A2-deficient mouse in which monophasic EAE had been induced.

The results are shown in FIG. 26. FIG. 26 shows that when the anti-CX3CR1 antibody was administered (CX3CR1), the late-stage EAE pathology improved more significantly than when the isotype (Isotype) was administered.

In addition, at day 22 and day 28 after the induction, the CNS of each mouse to which the anti-CX3CR1 antibody or the isotype thereof was administered was collected and CD4⁺ cells were separated. Regarding the CD4⁺ cells obtained, the percentages and the absolute numbers of Eomes⁺CD4⁺ cells or Eomes⁺CD4⁺ cells (Eomes-strong-positive, CD4-positive Th cells) with respect to the CD4⁺ cells were measured.

Figure 27:
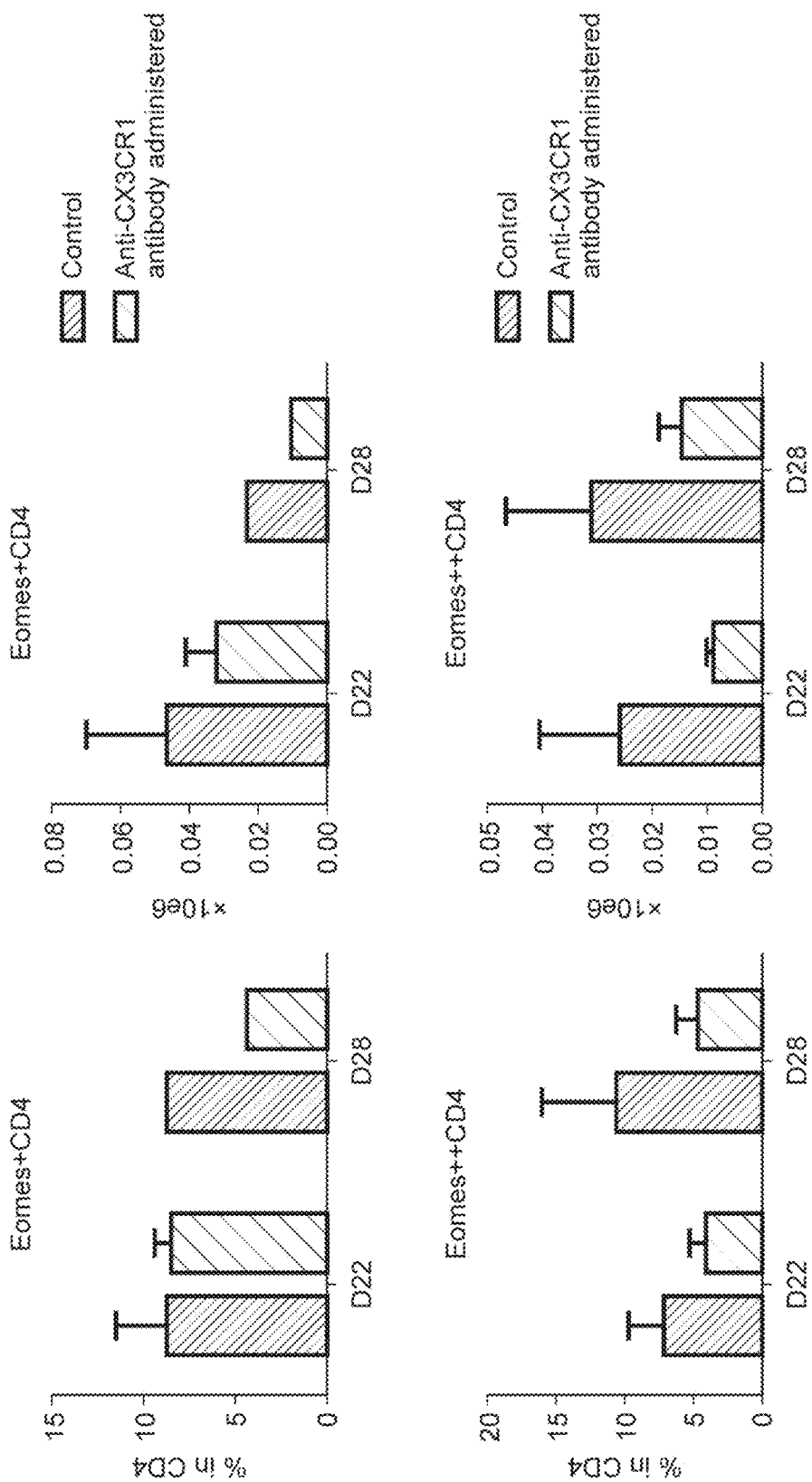
FIG. 27 is graphs showing the percentage of Eomes$^+$ CD4$^+$ Th cells with respect to CD4$^+$ Th cells when an anti-CX3CR1 antibody was administered to each NR4A2-deficient mouse in which monophasic EAE had been induced.

The results are shown in FIG. 27. As shown in FIG. 27, in any of the Eomes⁺CD4⁺ cells and the Eomes⁺⁺ CD4⁺ cells, the percentages and the absolute numbers of the Eomes-positive Th cells with respect to the CD4⁺ cells in the late-stage EAE pathology decreased significantly by the anti-CX3CR1 antibody dosing.

4. Suppression of Expression of Eomes Gene by Zbtb20-Specific siRNA Dosing (1) Change in Clinical Scores of EAE Pathology Into each NR4A2-deficient mouse in which monophasic EAE had been induced in a similar manner to the above 1.(3), atelocollagen matrix-stabilized Zbtb20-specific siRNA (manufactured by KOKEN Co., LTD.) or control scrambled siRNA (manufactured by KOKEN Co., LTD.) was intravenously injected at day 7 after the induction (corresponding to the early-stage EAE pathology). Then, the EAE pathology of each mouse was daily evaluated in accordance with the above-described EAE criteria.

Figures 28A, 28B:
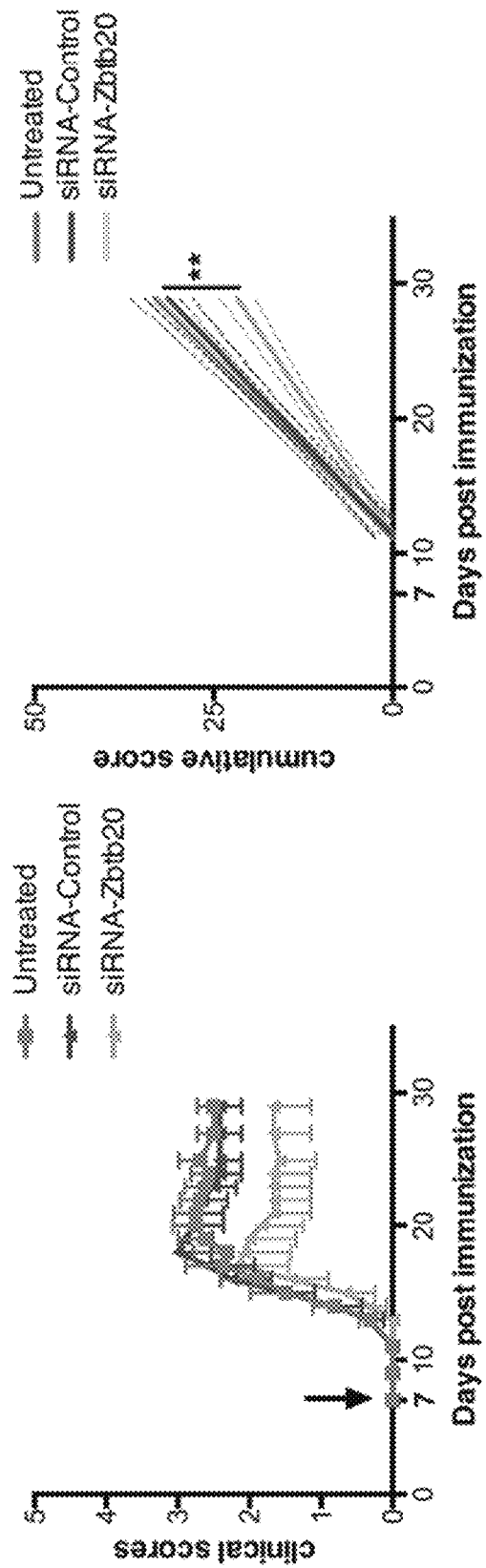
FIGS. 28A and 28B provide graphs showing the clinical scores in each EAE pathology mouse after Zbtb20-specific siRNA dosing.

The results are shown in FIG. 28. In the right graph of FIG. 28, the ordinate represents a cumulative clinical score. In each control scrambled siRNA-administered mouse, the clinical scores were substantially the same as in each intact mouse; by contrast, in each Zbtb20-specific siRNA-administered mouse, a marked decrease in the clinical scores was recorded. In the right graph of FIG. 28, the right graph shows, as a graph, the cumulative clinical scores; and the dashed lines each indicate 95% confidence interval.

(2) Suppression of Expression of Eomes or Zbtb20 Gene by Zbtb20-Specific siRNA Dosing The brain and the spinal cord were collected from each intact mouse, each Zbtb20-specific siRNA-administered mouse, or each control scrambled siRNA-administered mouse treated in a similar manner to the above 4.(1) were collected and CD4⁺ T cells and B cells were separated. The expression of Eomes or Zbtb20 gene in the CD4⁺ T cells or B cells, respectively, from each mouse group obtained was analyzed with a flow cytometer. As antibodies used at the detection were an anti-CD4 antibody (manufactured by Biolegend, Inc.), an anti-Eomes antibody (manufactured by eBioscience, Inc.), an anti-CD19 antibody (manufactured by Biolegend, Inc.), and an anti-Zbtb20 antibody (manufactured by Becton Dickinson, Inc.).

Figures 29A, 29B:
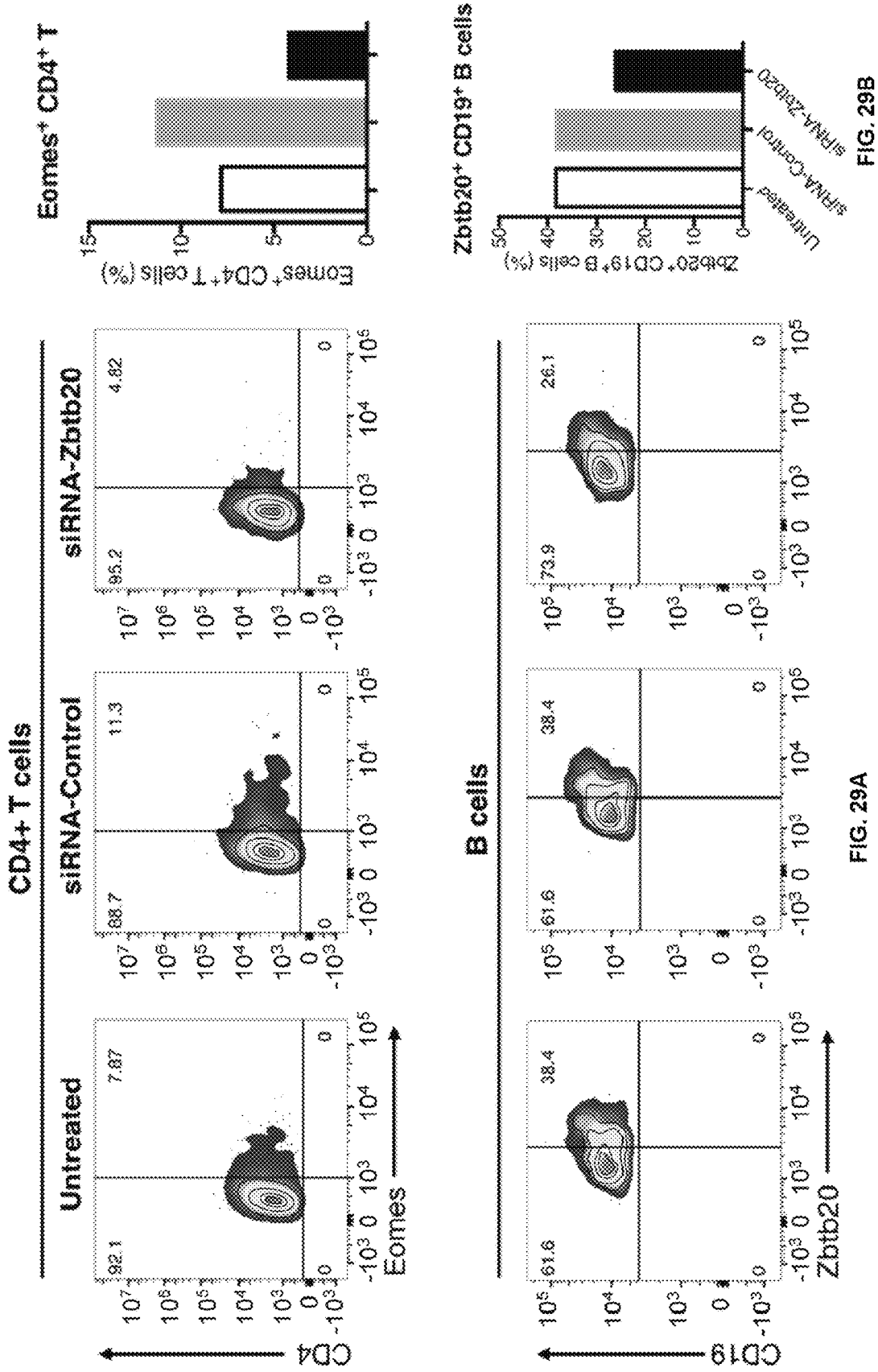
FIG. 29 is graphs showing expression of Eomes protein (FIG. 29A) or Zbtb20 protein (FIG. 29B) after Zbtb20-specific siRNA dosing.

The results are shown in FIG. 29. As shown in FIG. 29(a), it was observed that the expression of Eomes gene in the CD4⁺ T cells and the expression of Zbtb20 gene in the B cells in each Zbtb20-specific siRNA-administered mouse were both markedly suppressed. FIG. 29(b) shows, as a graph for comparison, the percentage of Eomes- or Zbtb20-expressing cells in each mouse group.

(3) Suppression of Expression of Prolactin Gene by Zbtb20-Specific siRNA Dosing

By using each intact mouse, each Zbtb20-specific siRNA-administered mouse, or each control scrambled siRNA-administered mouse treated in a similar manner to the above 4.(1), antigen-presenting cells were separated from the CNS of each mouse with the late-stage EAE pathology. Next, CD19⁻CD45$^{hi}$ non-B/class II⁺ antigen-presenting cells were purified from the obtained antigen-presenting cells by sorting by FACS using a FACS ARIA II (manufactured by BD Cytometry Systems, Inc.). The purified cells were transfected with the Zbtb20-specific siRNA or the control scrambled siRNA and cultured for 24 h in the presence of LPS; and the Zbtb20 or prolactin (Prl) expression levels were then measured by using a quantitative real-time PCR assay. As antibodies used at the detection were an anti-CD4 antibody (manufactured by Biolegend, Inc.), an anti-Eomes antibody (manufactured by eBioscience, Inc.), an anti-CD19 antibody (manufactured by Biolegend, Inc.), and an anti-CD45 antibody (manufactured by Biolegend, Inc.).

Figure 30:
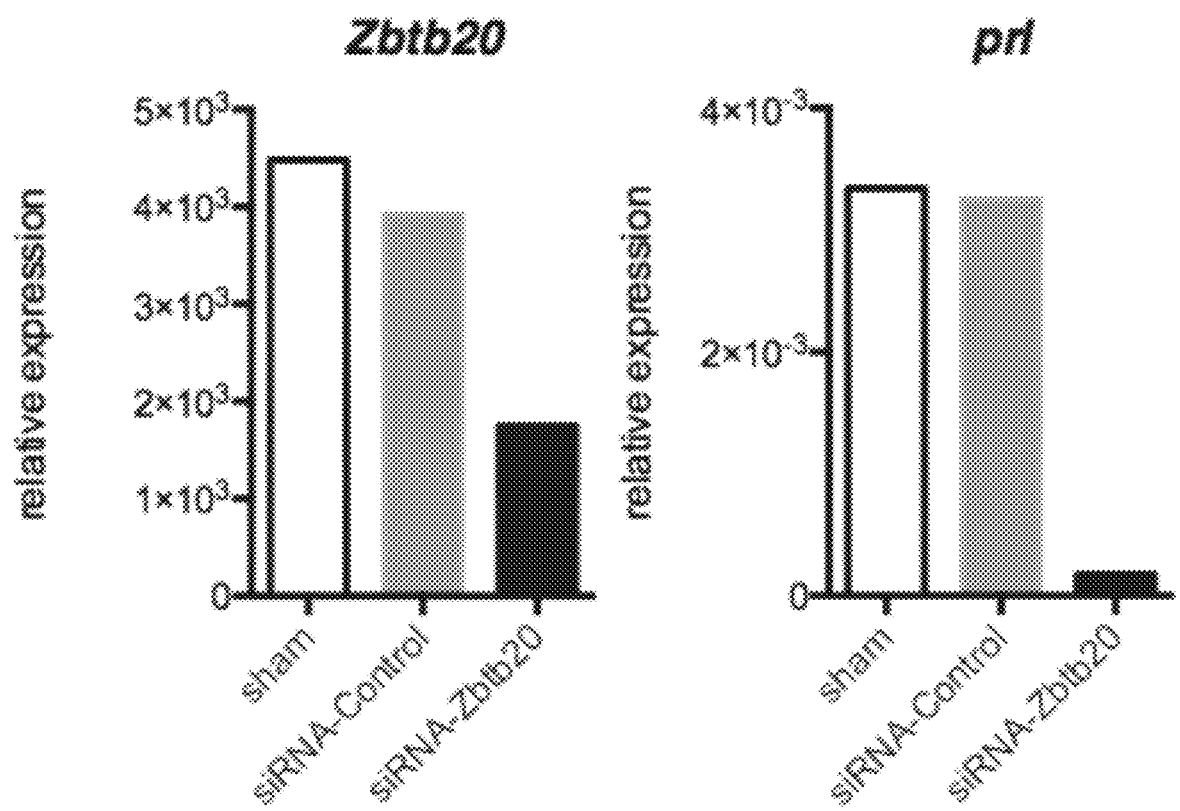
FIG. 30 is graphs showing expression of prolactin gene or Zbtb20 gene after Zbtb20-specific siRNA dosing.

The results are shown in FIG. 30. It was observed that the dosing of the Zbtb20-specific siRNA caused the Zbtb20 gene and Prl gene expression levels to decrease markedly.

5. Suppression of Expression of Eomes Gene by Anti-CD20 Antibody Dosing (1) Change in Clinical Scores of EAE Pathology Into each NR4A2-deficient mouse in which monophasic EAE had been induced in a similar manner to the above 1.(3), an anti-CD20 antibody or control IgG was intravenously injected 7 days before or at day 13 after the induction; and the EAE pathology of each mouse was daily evaluated in accordance with the above-described EAE criteria.

Figure 31A:
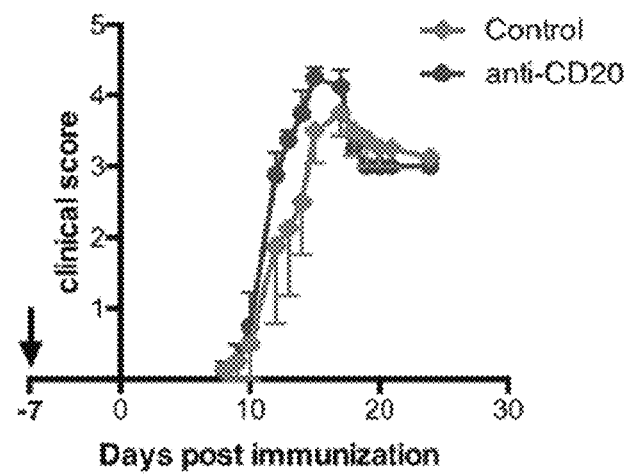
FIGS. 31A and 31B are graphs showing the clinical scores in each EAE pathology mouse after anti-CD20 antibody dosing.
Figure 31B:
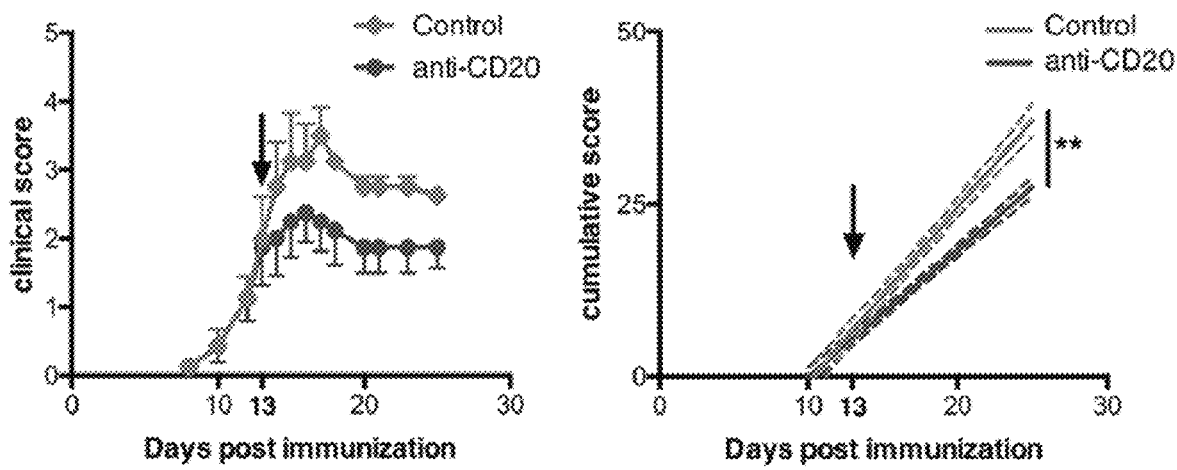

The results are shown in FIGS. 31(a) and (b). Each arrow in FIGS. 31(a) and (b) denotes the day when the antibody was administered. FIG. 31(a) shows the results obtained when the antibody was administered 7 days before the induction; and FIG. 31(b) shows the results obtained when the antibody was administered at day 13 after the induction. As shown in FIG. 31(b), the clinical scores improved markedly by dosing the anti-CD20 antibody at day 13 after the induction. The right graph of FIG. 31(b) shows, as a graph, the cumulative clinical scores; and the dashed lines each indicate 95% confidence interval.

(2) Suppression of Expression of Eomes or Zbtb20 Gene by Anti-CD20 Antibody

The brain and the spinal cord were collected from each intact mouse, each anti-CD20 antibody-administered mouse, or each control IgG-administered mouse treated in a similar manner to the above 5.(1), and CD4+ T cells and B cells were separated. The expression of Eomes or Zbtb20 gene in the CD4+ T cells or B cells, respectively, from each mouse group obtained was analyzed with a flow cytometer. As antibodies used at the detection were an anti-CD4 antibody (manufactured by Biolegend, Inc.), an anti-Eomes antibody (manufactured by eBioscience, Inc.), an anti-CD20 antibody (manufactured by Biolegend, Inc.), an anti-CD45 antibody (manufactured by Biolegend, Inc.), and an anti-Zbtb20 antibody (manufactured by Becton Dickinson, Inc.).

Figure 31C:
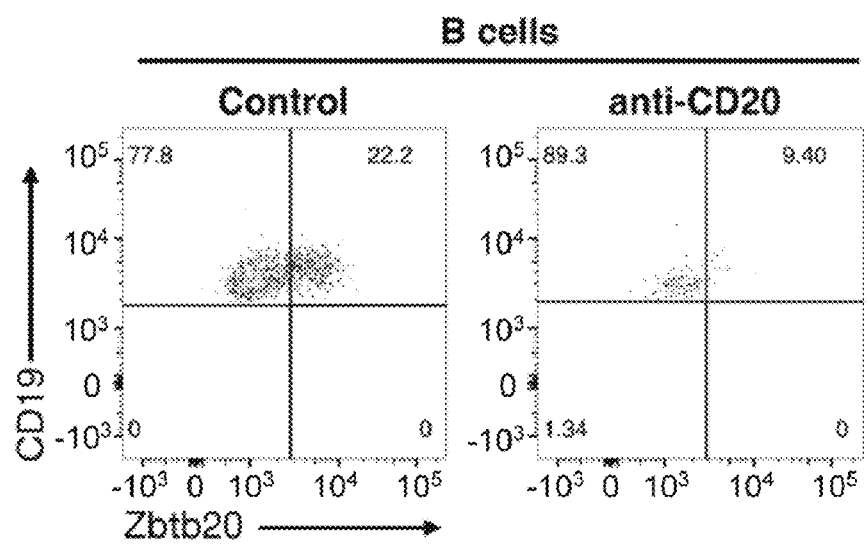
FIG. 31C is graphs showing Zbtb20 protein expression after anti-CD20 antibody dosing.
Figure 32:
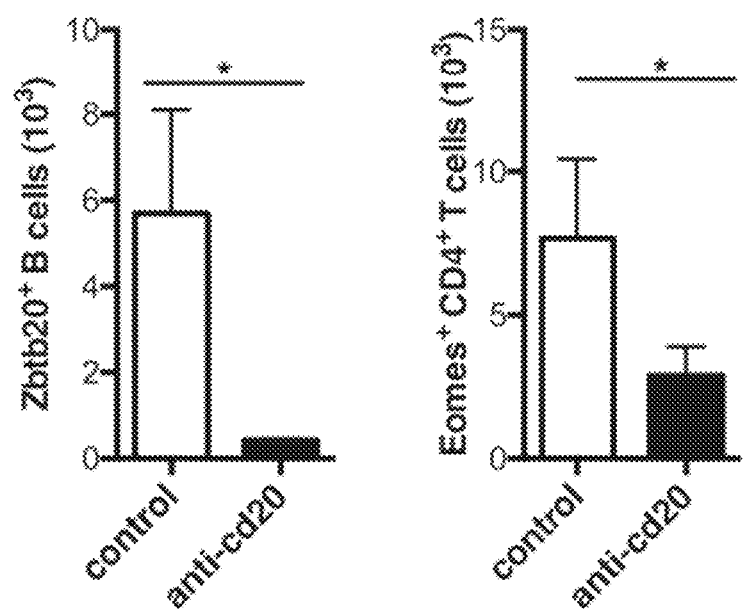
FIG. 32 is graphs showing expression of Eomes protein or Zbtb20 protein after anti-CD20 antibody dosing.

The results are shown in FIGS. 31(c) and 32. As shown in FIG. 31(c), it was observed that the expression of Eomes gene in the CD4+ T cells and the expression of Zbtb20 gene in the B cells in each anti-CD20 antibody-administered mouse were both suppressed markedly. FIG. 32 shows, as a graph for comparison, the percentage of Eomes- or Zbtb20-expressing cells in each mouse group.

6. Changes in Zbtb20 Gene Expression by Various Cytokines (1) Changes in Zbtb20 Gene Expression by Various Cytokines Spleen-derived CD19+ B cells were isolated and purified by sorting by FACS using a FACS ARIA II (manufactured by BD Cytometry Systems, Inc.). The purified B cells were cultured for 24 h in the presence of LPS and in the co-presence or absence of each cytokine designated in FIG. 33(a). After the culturing, the expression levels of Zbtb20 gene in the respective cells were measured. As antibodies used at the detection were an anti-CD19 antibody (manufactured by Biolegend, Inc.) and an anti-Zbtb20 antibody (manufactured by Becton Dickinson, Inc.).

Figure 33A:
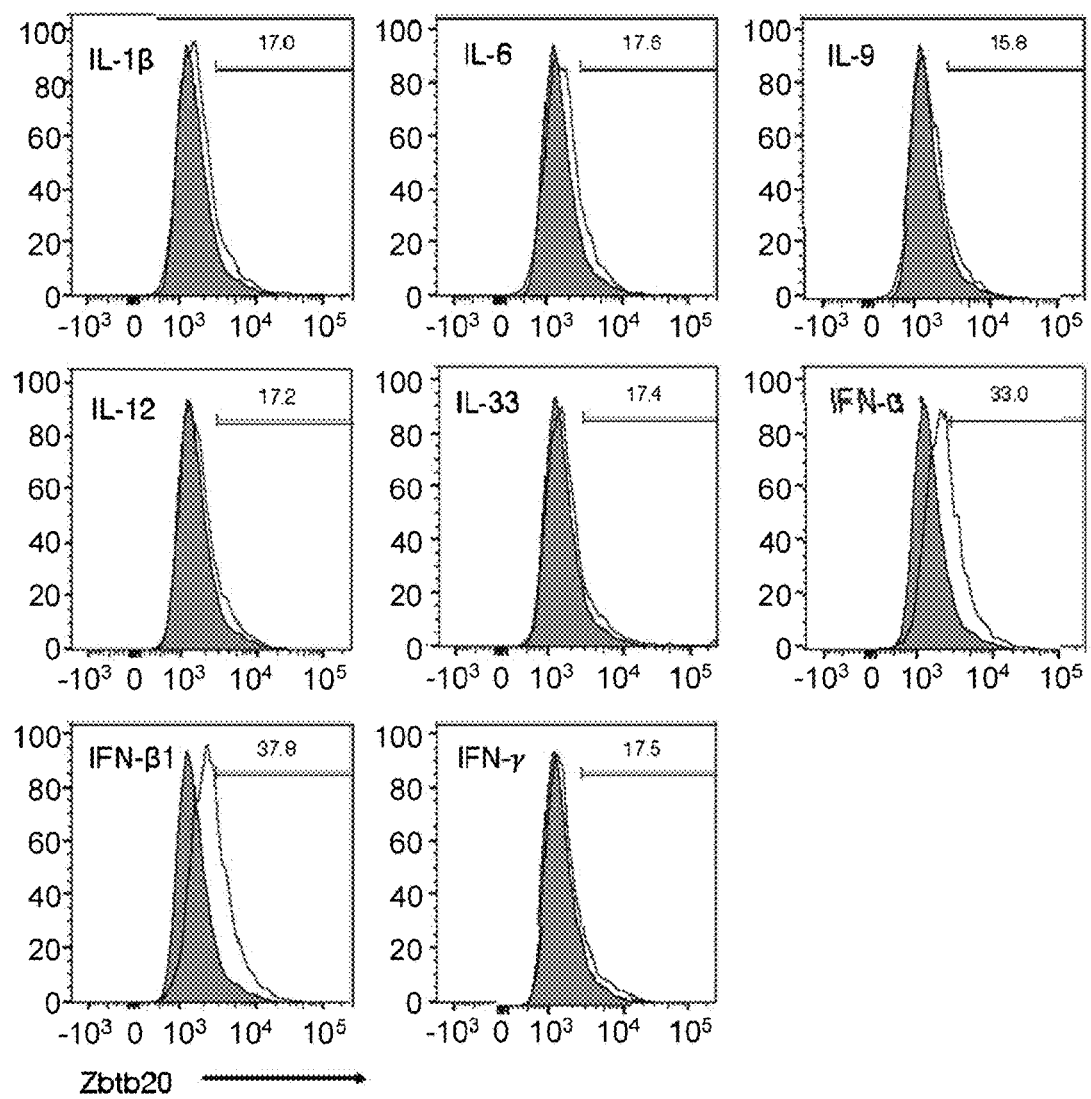
FIG. 33A shows the expression level of Zbtb20 gene in the cells cultured in the absence of each cytokine.
Figure 33B:
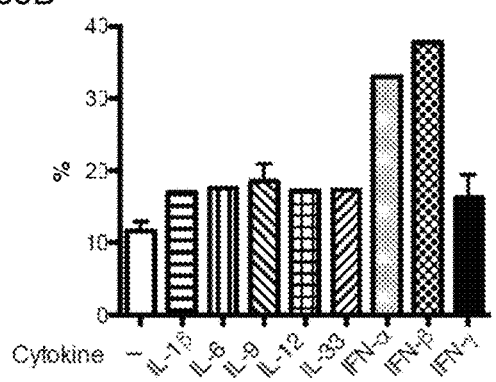
FIG. 33B shows the percentage of Zbtb20$^+$ cells under each condition.
Figure 34:
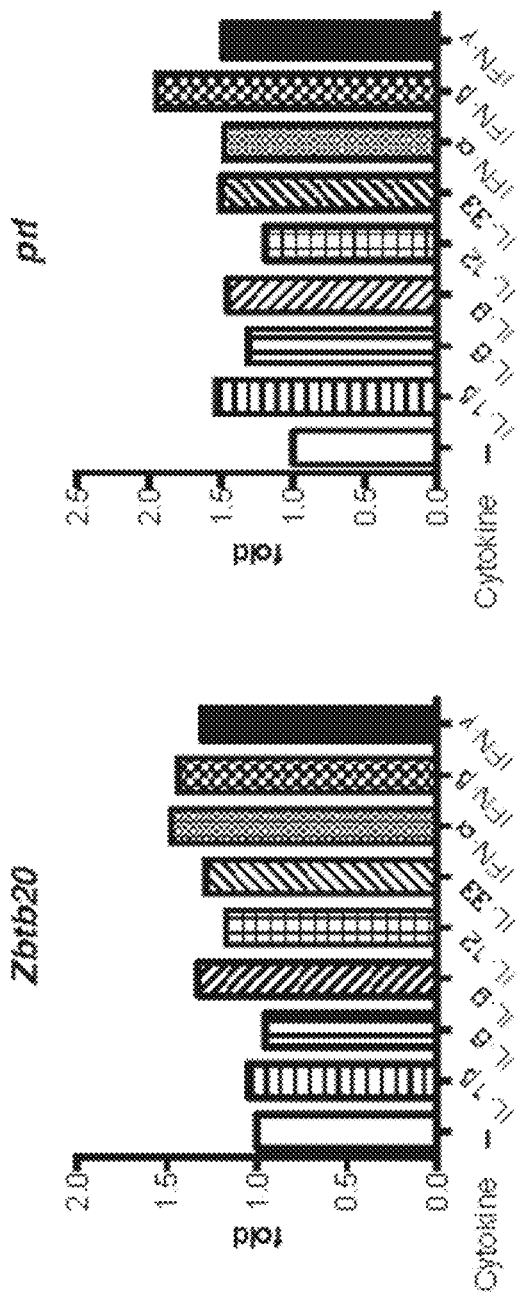
FIG. 34 is graphs showing expression of Zbtb20 gene or prolactin gene under culturing in the presence of each different cytokine.

The results are shown in FIGS. 33 and 34. In FIG. 33(a), the gray graphs each indicate the expression level of Zbtb20 gene in the cells cultured in the absence of each cytokine; and the black line graphs each indicate the expression level in the case of culturing in the co-presence of each different cytokine. After the culturing in the co-presence of each cytokine designated, it was observed that the expression of Zbtb20 gene increased; and an increase in the expression of Zbtb20 gene by culturing in the co-presence of IFNα or IFNβ1 was the most remarkable. FIG. 33(b) shows, as a graph, each percentage of Zbtb20+ cells under each condition. FIG. 34 shows how many folds each percentage of the Zbtb20+ cells or Prl+ cells increased in the case of culturing in the co-presence of each different cytokine compared to the case of culturing in the absence of the cytokine.

(2) Changes in Each Different Cytokine Expression During Course of Progression of EAE Pathology–1

The CSF and plasma were collected from each mouse at each progression stage (early-stage EAE pathology, mid-stage EAE pathology, or late-stage EAE pathology) and the expression level of each different cytokine was measured by using a Luminex system. In addition, the expression levels of each of type 1 interferons (IFNα2, IFNβ1), IL-6, IL-9, and Cxcl13 in CNS-derived B cells, pDCs, or microglia were likewise measured by using a quantitative real-time PCR assay. To detect IFNα2 and IFNβ1, ProcartaPlex Mouse IFNa/b (manufactured by ThermoFisher Scientific, Inc.) was used. To detect other cytokines, BioPlex Pro Cytokine GI 23-plex panel and BioPlex Pr Cytokine GIII TH17 8-plex B panel (manufactured by Bio-Rad, Inc.) were used.

Figure 35:
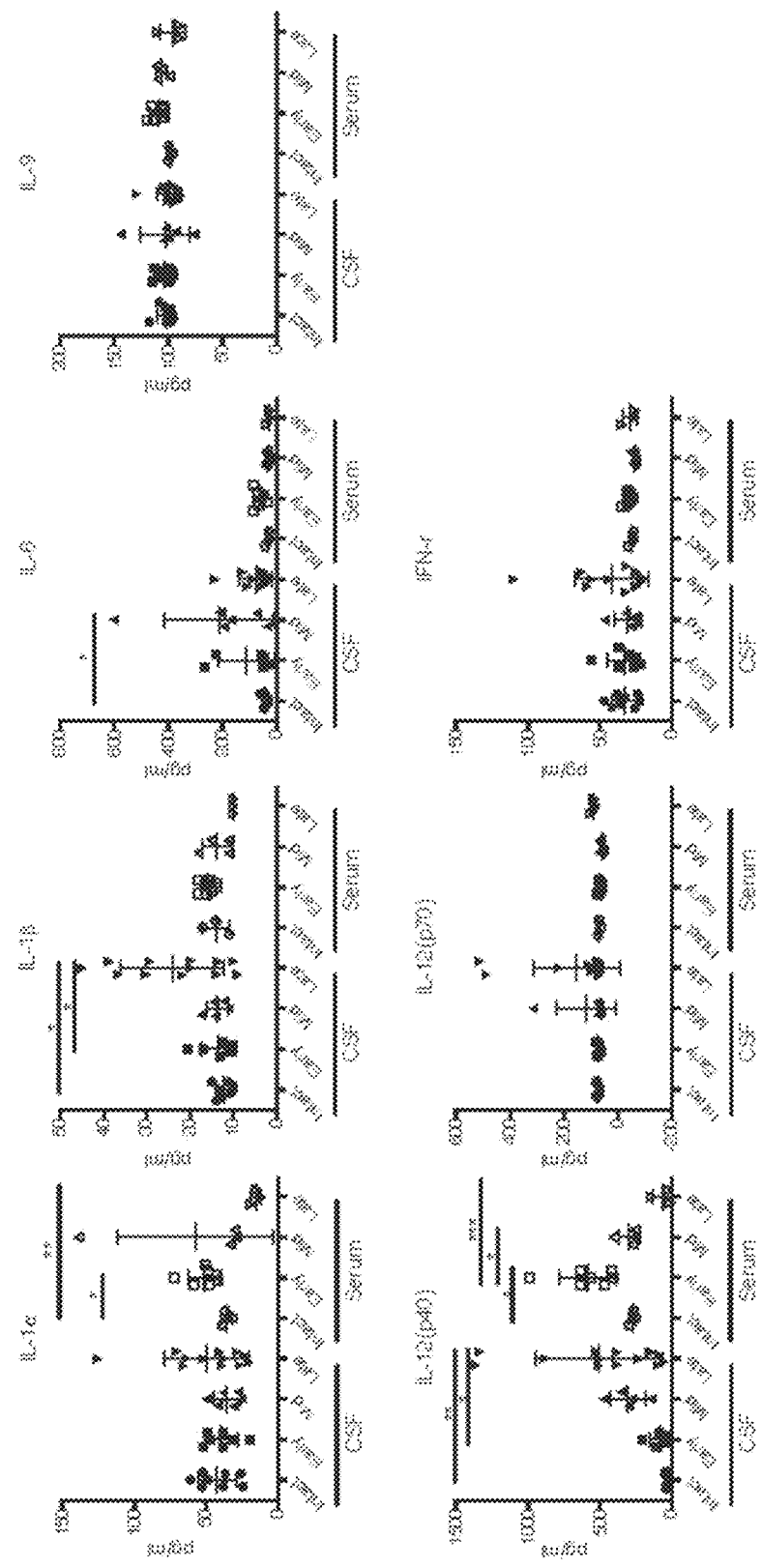
FIG. 35 is graphs showing the changes in expression of each different cytokine during the course of progression of EAE pathology.
Figure 36A:
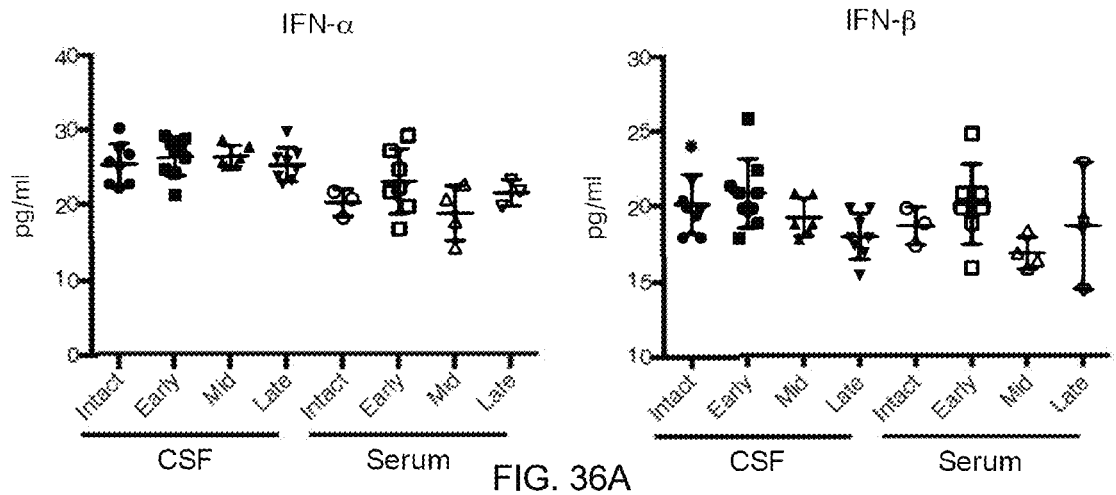
FIG. 36A shows IFN-α or IFN-β expression levels.
Figure 36B:
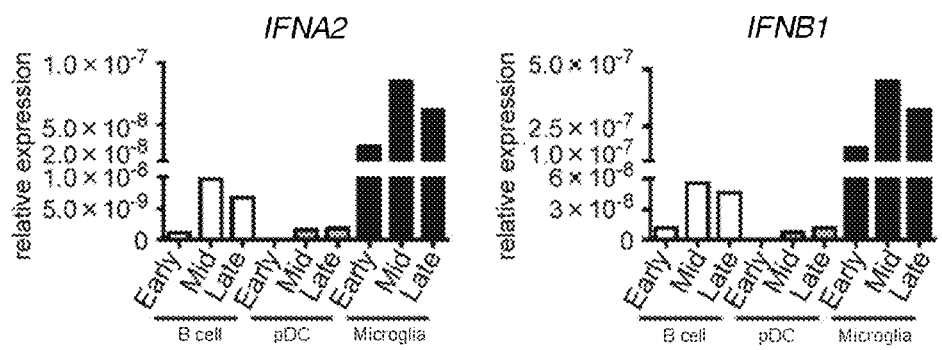
FIG. 36B shows IFNα2 or IFNβ1 expression in CNS-derived B cells, pDCs, or microglia.
Figure 36C:
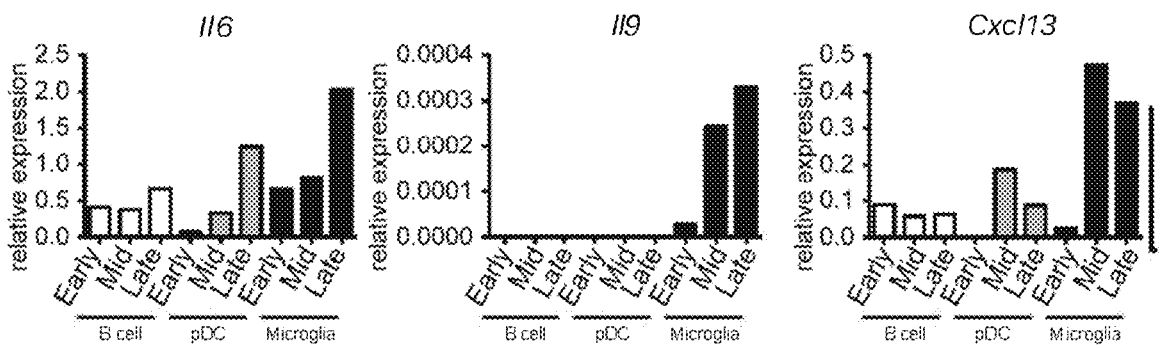
FIG. 36C shows IL-6, IL-9, and Cxcl13 expression levels in CNS-derived B cells, pDCs, or microglia.

The results are shown in FIGS. 35 and 36. FIG. 35 shows IL-1α, IL-1β, IL-6, IL-9, IL-12 (p40), IL-12 (p70), and IFN-γ expression levels. FIG. 36(a) shows the IFN-α or IFN-β expression levels. FIG. 36(b) shows an amount of the IFNα2 or IFNβ1 expression in the CNS-derived B cells, pDCs, or microglia. FIG. 36(c) shows an amount of the IL-6, IL-9, or Cxcl13 expression in the CNS-derived B cells, pDCs, or microglia. As shown in FIGS. 36(b) and (c), it was observed that the amounts of expression of IFN-α2, IFN-β1, and IL-9 in microglia at the time of mid-EAE pathology increased markedly.

(3) Effects of Microglia Derived from Each Mouse with Late-Stage EAE Pathology on Zbtb20 Expression CD19+ B cells were sorted from the spleen of each intact mouse of similar genetic strain by FACS and were co-cultured for 24 h with microglial cells derived from each intact mouse or each mouse with the late-stage EAE pathology. The amounts of expression of Zbtb20 gene in the cultured B cells were measured with a flow cytometer. In addition, the B cells were purified by sorting by FACS, and Zbtb20 and Prl RNA levels were detected by using a real-time PCR assay. As antibodies used at the detection were an anti-CD19 antibody (manufactured by Biolegend, Inc.) and an anti-Zbtb20 antibody (manufactured by eBioscience, Inc.).

Figure 37A:
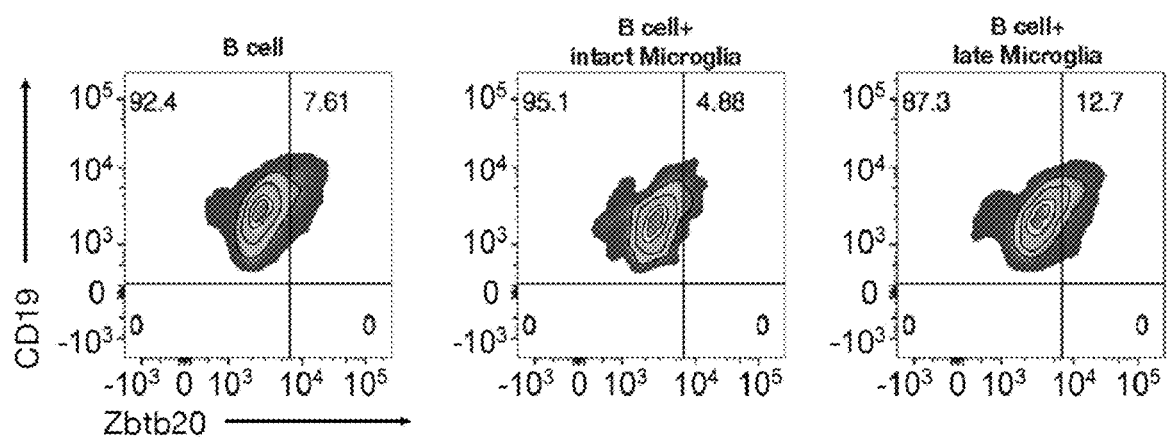
FIG. 37A shows levels of Zbtb20 expression in CD19$^+$ B cells co-cultured with microglia of each mouse with the late-stage EAE pathology.
Figure 37B:
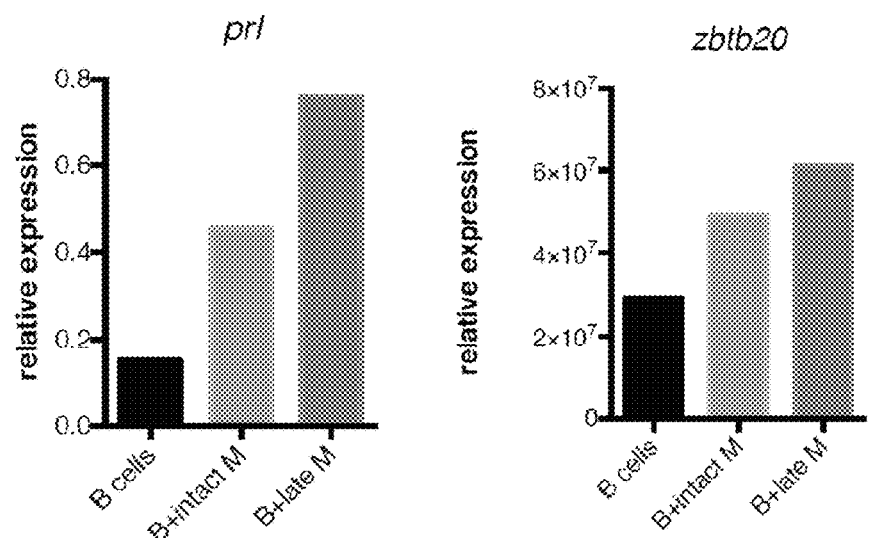
FIG. 37B shows levels Zbtb20 and Pr1 RNA levels in the cultured cells.

The results are shown in FIG. 37. As shown in FIG. 37(a), it was observed that the expression of Zbtb20 gene was enhanced markedly when the CD19+ B cells were co-cultured with microglia of each mouse with the late-stage EAE pathology. In addition, as shown in FIG. 37(b), it was observed that the Zbtb20 and Prl RNA levels also increased relatively.

(4) Changes in Each Different Cytokine Expression During Course of Progression of EAE Pathology The CSF and plasma were collected from each intact mouse or each mouse with each progression stage of EAE pathology, and a Luminex system was used to measure the protein levels of various cytokines (IL-2, IL-4, IL-3, IL-5, IL-10, IL-13, IL-17, G-CSF, GM-CSF, TNF-α, Eotaxin, KC, MCP-1, MIP-1b, RANTES, and MIP-1a). For detection, BioPlex Pro Cytokine GI 23-plex panel and BioPlex Pr Cytokine GIII TH17 8-plex B panel (manufactured by Bio-Rad, Inc.) were used.

Figure 38:
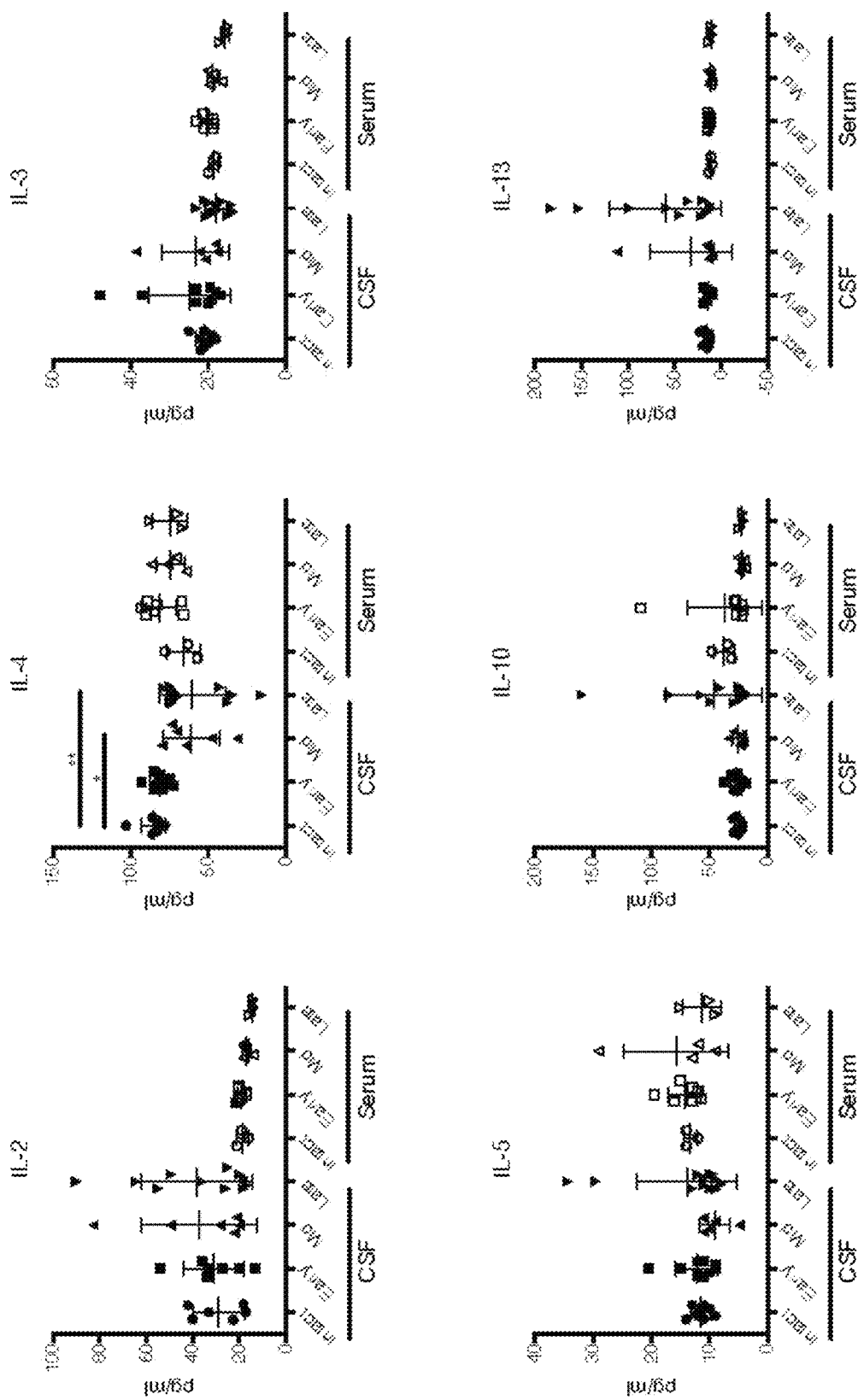
FIG. 38 is graphs showing the changes in expression of each different cytokine during the course of progression of EAE pathology.
Figure 39:
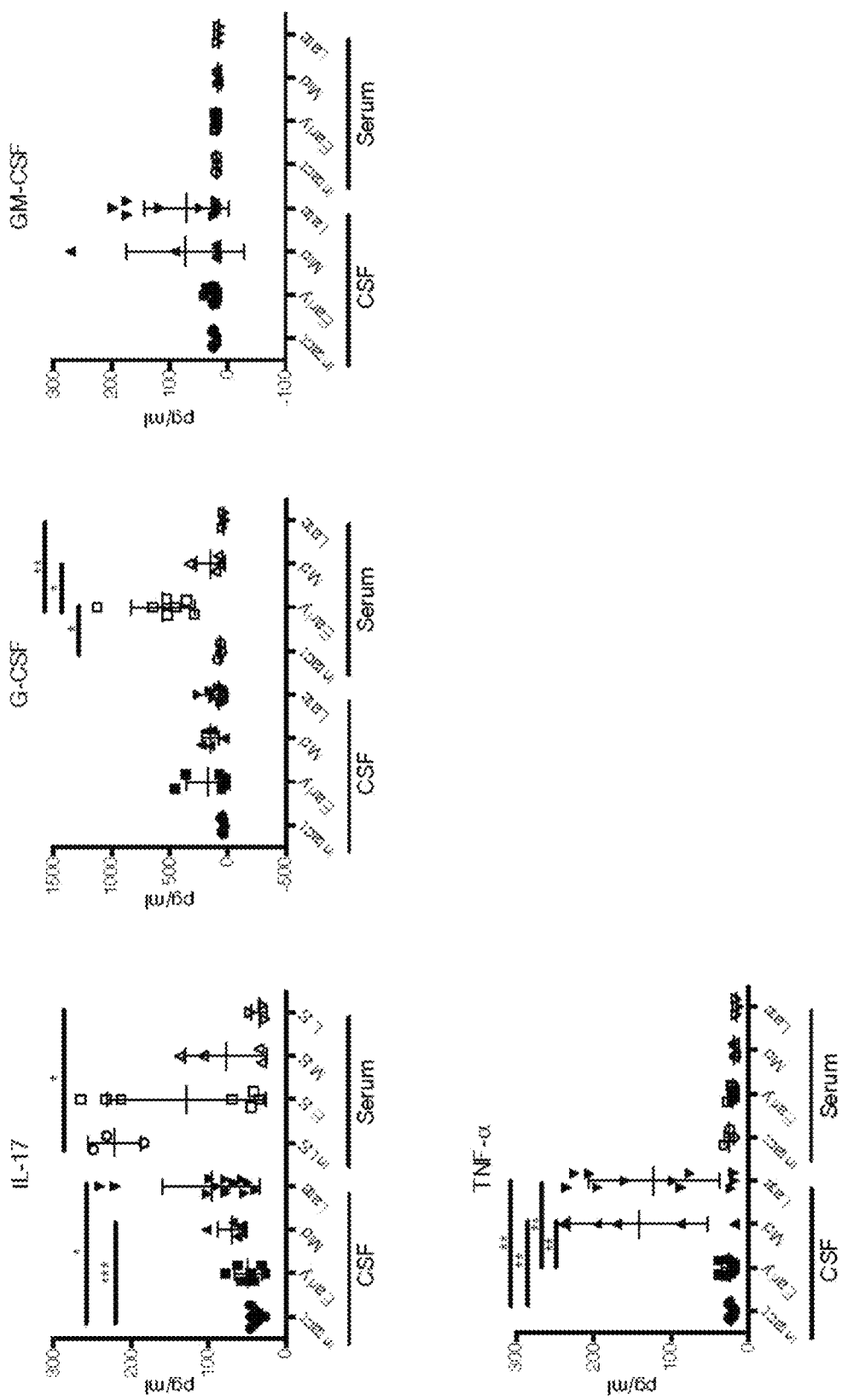
FIG. 39 is graphs showing the changes in expression of each different cytokine during the course of progression of EAE pathology.
Figure 40:
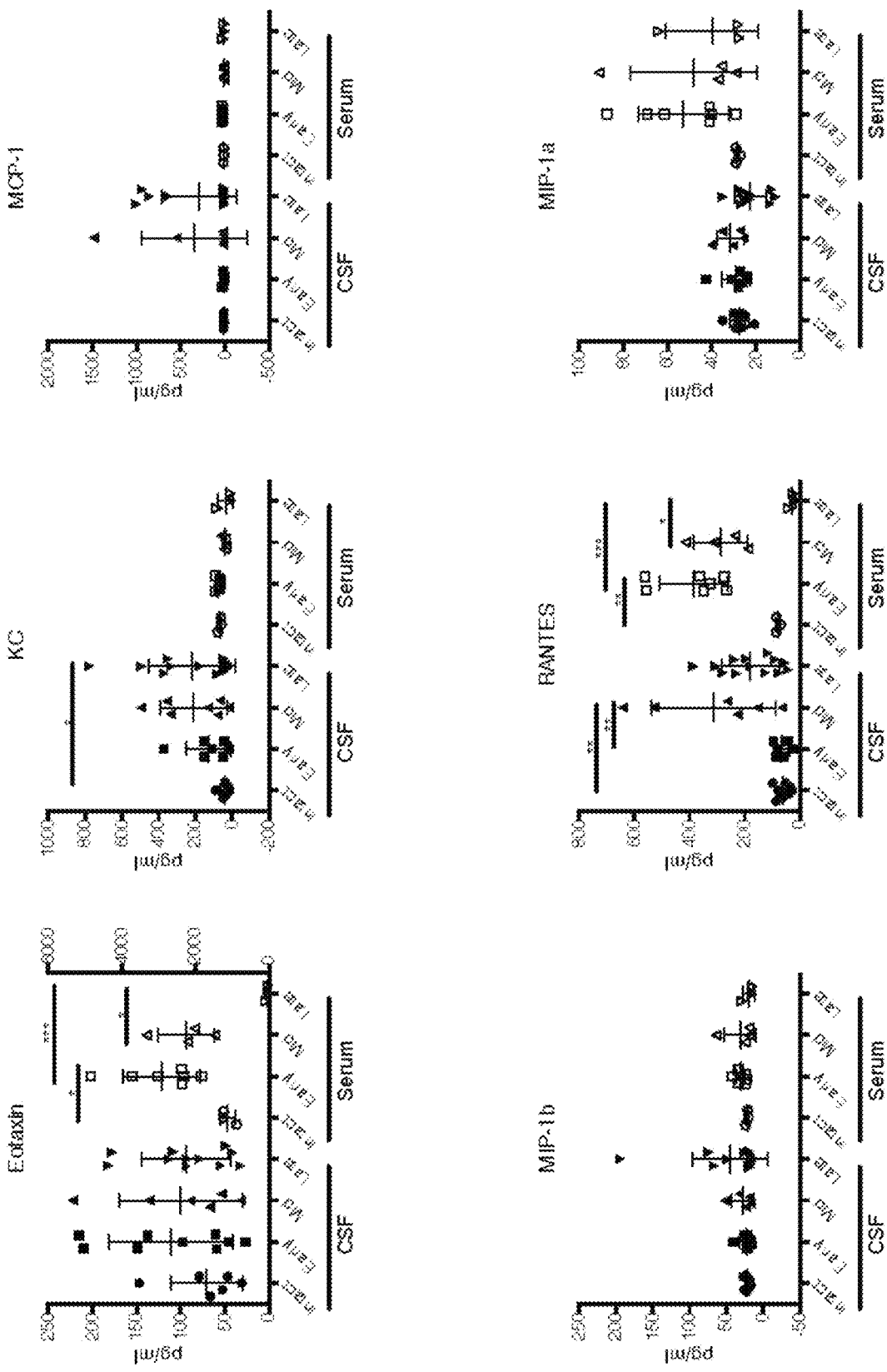
FIG. 40 is graphs showing the changes in expression of each different chemokine during the course of progression of EAE pathology.

The results are shown in FIGS. 38 to 40.

The invention claimed is:

1. A method for treating progressive multiple sclerosis (MS) in a subject suffering from progressive MS, by decreasing Eomes-expressing T helper (Th) cells in the subject, the method comprising:
   administering, to the subject, an anti-CX3CR1 antibody or an antigen-binding fragment thereof.

* * * * *